United States Patent
Leer et al.

(12) 
(10) Patent No.: US 6,506,389 B2
(45) Date of Patent: *Jan. 14, 2003

(54) ADHERENCE FACTORS OF NON PATHOGENIC MICROORGANISMS AND APPLICATIONS THEREOF FOR SCREENING MICROORGANISMS FOR SPECIFIC PROBIOTIC PROPERTIES; NOVEL PHARMACEUTICAL COMPOSITIONS AND FOOD ADDITIVES COMPRISING SUCH MICROORGANISMS AND ADHERENCE FACTORS

(75) Inventors: Robert Jan Leer, Voorburg; Pieter Hendrik Pouwels, Rijswijk, both of (NL); Patricia Lynne Conway, Le Perouse (AU)

(73) Assignee: Nederlandse Organisatie voor Toegepast-Natuurwetenschappelijk Onderzoek (TNO), Delft (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,755
(22) PCT Filed: Oct. 21, 1996
(86) PCT No.: PCT/NL96/00409
 § 371 (c)(1),
 (2), (4) Date: Sep. 30, 1998
(87) PCT Pub. No.: WO97/14802
 PCT Pub. Date: Apr. 24, 1997

(65) Prior Publication Data
 US 2001/0018048 A1 Aug. 30, 2001

(51) Int. Cl.$^7$ ...................... A61K 39/07; A61K 39/385; A61K 39/38; C07H 21/04; C12D 21/04
(52) U.S. Cl. ................................ 424/246.1; 424/184.1; 424/185.1; 424/193.1; 536/23.1; 536/23.5; 435/69.1; 435/69.7; 435/252.1; 435/252.3; 435/7.1; 435/7.2; 530/300; 530/350
(58) Field of Search .............................. 435/69.7, 252.3, 435/252.1, 69.1, 7.1, 7.2; 530/300, 350; 424/246.1, 184.1, 193.1; 536/23.1, 23.5

(56) References Cited
FOREIGN PATENT DOCUMENTS
WO  WO 90/09398  8/1990

OTHER PUBLICATIONS

Roos et al., A Collagen Binding Protein From *Lactobacillus reuteri* Is Part Of An ABC Transporter System?; Fems Microbiology Letters 144; 33–38, 1996.*

Abstract: Short Protocols in Molecular Biology, 1995.*
P. Aleljung et al., "Purification of collagen–binding proteins of *Lactobacillus reuteri* NCIB 11951", pp. 231–236, Current Microbiology, vol. 28, No. 4, 1994.
T. Toba et al., "A collagen–binding S–layer protein in *Lactobacillus crispatus*", pp. 2467–2471, Applied and Environmental Microbiology, vol. 61, No. 7, Jul. 1995.
J.D. Greene et al., "Factors involved in adherence of lactobacilli to human caco–2 cells", pp. 4487–4494, Applied and Environmental Microbiology, vol. 60, No. 12, Dec. 1994.
D.W.S. Harty et al., "Pathogenic potential of lactobacilli", pp. 179–189, International Journal of Food Microbiology, vol. 24, Dec. 1994.
A. Henriksson et al., "Adhesion to porcine squamous epithelium of saccharide and protein moieties of *Lactobacillus fermentum* strain 104–S", pp. 2657–2661, Journal of General Microbiology, vol. 138, 1992.
Francesco Rodriguez et al., "An operon encoding a novel ABC–type transport system in *Bacillus subtilis*", pp. 1781–1784, Microbiology, vol. 141, No. 7, Jul. 1995.
Byung–Ha Oh et al., "The bacterial periplasmic histidine–binding protein", pp. 4135–4143, The Journal of Biological Chemistry, vol. 269, No. 6, Feb. 11, 1994.
Amnon Wolf et al., "Structure/function analysis of the periplasmic histidine–binding protein", pp. 16097–16106, The Journal of Biological Chemistry, vol. 270, No. 27, Jul. 7, 1995.

* cited by examiner

Primary Examiner—Lynette R. F. Smith
Assistant Examiner—Padma Baskar
(74) Attorney, Agent, or Firm—Young & Thompson

(57) ABSTRACT

A protein obtainable from a non pathgenic microorgansim, said protein having mucosa binding promoting activity and a molecular weight of 20–40 kD is disclosed. Application of such a protein or a peptide derived therefrom in a method of screening non pathogenic microorganisms for a microorganism capable of specifically binding mucosa, said method comprising detection in a manner known per se of the presence of a particular protein on or in a microorganism or in a culture of microorganisms, said particular protein being the already defined protein. Kits suitable for such a screening method are also disclosed. Use of a component selected from the group of components comprising a protein or peptide as defined; an expression vector comprising nucleic acid encoding such protein or peptide; a recombinant microorganism or a part of said microorganism expressing such protein or peptide, said part expressing mucosa binding promoting activity; a non pathogenic microorganism capable of expressing such protein or peptide or a part of said microorganism, said part expressing mucosa binding promoting activity as pharmaceutically active component in a pharmaceutical composition for prophylaxis and/or treatment of disease or illness associated with a mucosa colonizing pathogenic microorganism. Use of such components as food additive and compositions comprising such components are described.

13 Claims, 9 Drawing Sheets fig-1a
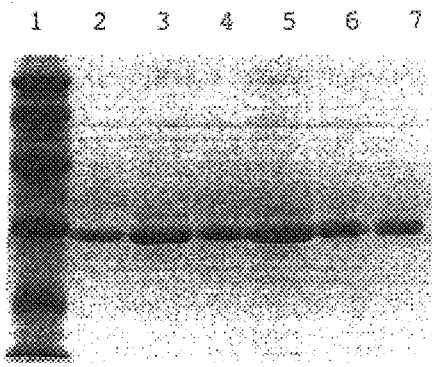
fig-1b
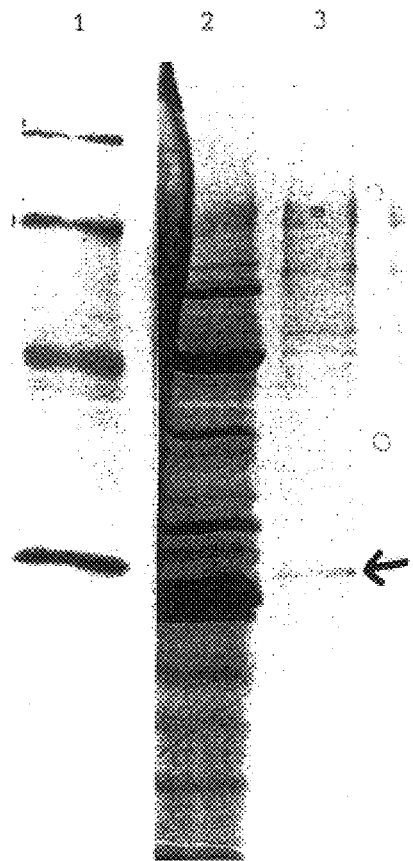
fig-1c

Fig-2

```
  1  CTGCAGGAAT CACAAGTGTT TCTGCTGCTT CAGCTGTTAA TTCAGAATTA

51  GTTCATAAGG GAGAATTAAC AATTGGTCTT GAGGGAACGT ACTCTCCGTA

101  CTCTTATCGT AAAAATAACA AATTAACTGG CTTTGAAGTA GATCTTGGTA

151  AAGCAGTTGC TAAAAAGATG GGCTTAAAAG CTAACTTTGT ACCAACTAAA

201  TGGGATTCGC TAATTGCCGG TCTTGGTTCA GGTAAGTTTG ATGTAGTAAT

251  GAACAACATT ACACAGACAC CTGAACGGGC CAAGCAATAT AATTTCTCTA

301  CCCCATATAT CAAGTCCCGG TTTGCATTAA TTGTTCCTAC TGATAGTAAC

351  ATCAAAAGCT TGAAGAATAT TAAAGGCAAG AAGATTATTG CTGGTACGGG

401  AACTAATAAT GCGAATGTGG TAAAAAAATA TAAGGGTAAC CTTACACCAA

451  ATGGCGATTT TGCTAGTTCC TTAGATATGA TCAAGCAAGG TCGGGCTGCC

501  GGGACAATTA ACTCCCGTGA AGCTTGGTAC GCTTACAGCA AGAAGAACAG

551  TACTAAGGGT CTCAAGATGA TTGATGTTTC TAGTGAACAA GATCCAGCTA

601  AGATTTCAGC ACTTTTTAAC AAGAAAGATA CTGCTATTCA ATCTTCCTAC

651  AACAAGGCAC TTAAGGAACT TCAACAAGAC GGAACAGTCA AGAAGCTATC

701  TGAAAAGTAC TTCGGTGCAG ATATTACTGA ATAATTAAAA AAGATCT
```

Fig-3

```
  1  AGITSVSAAS AVNSELVHKG ELTIGLEGTY SPYSYRKNNK LTGFEVDLGK

51  AVAKKMGLKA NFVPTKWDSL IAGLGSGKFD VVMNNITQTP ERAKQYNFST

101  PYIKSRFALI VPTDSNIKSL KNIKGKKIIA GTGTNNANVV KKYKGNLTPN

151  GDFASSLDMI KQGRAAGTIN SREAWYAYSK KNSTKGLKMI DVSSEQDPAK

201  ISALFNKKDT AIQSSYNKAL KELQQDGTVK KLSEKYFGAD ITE*
```

Fig-4.1

```
             1                                                                    50
Adhesin      .......... ........AG  ITSVSAASAV  NSELVHKGEL  TIGLEGTYSP
LapT         .......... ..........  MKKTLLTLLF  GCVVTAQAQD  IIVMEPSYPP
Peb1         MVFRKSLLKL  AVFALGACVA  FSNANAAEGK  LESIKSKGQL  IVGVKNDVPH
                         : * A                  : KG:L *IG:***Y:P 51                                                                   100
Adhesin      YSY.RK.NNK  LTGFEVDLGK  AVAKKM...G  LKANFVPTKW  DSLIAGLGSG
LapT         FEMTEE.KGE  IIGFDVDIAN  AICKEM...N  ANCTFHSQPF  DSLIQSLQK
Peb1         YALLDQATGE  IKGFEVDVAK  LLAKSILGDD  KKIKLVAVNA  KTRGPLLDNG
             Y::   : *:*  :*GFEVD::K   :AK*M       K**:V:  :  DSLI*:L  G 101                                                                  150
Adhesin      KFDVVMNNIT  QTPERAKQYN  FSTPYIKSRF  ALIVPTDSNI  KSLKNIKGKK
LapT         QFDAAISGMG  ITEPRKKQVL  FSEPYFPSSA  AFIAKKDTDF  AKVKTI...G
Peb1         SVDAVIATFT  ITPERKRIYN  FSEPYYQDAI  GLLVLKEKKY  KSLADMKGAN
             *FD:V:**:T  TPER KQYN  FS*PY::S    ALIV *D*::  KSLK:IKG :

151                                                                  200
Adhesin      I...IAGTGT  NNANVVKKY.  ..KGNLTPNG  DFASSLDMIK  QGRAAGTINS
LapT         V...QNGTTY  QHYLAKEKK.  ..EYNVKSYA  SYQNAILDVQ  NGRIDAIFGD
Peb1         IGVAQAATTK  KAIGEAAKKI  GIDVKFSEFP  DYPSIKAALD  AKRVDAFSVD
             I   AGT:  :*      K       * N:** : D:*S*:  :* *GR:*: : *
```

Fig-4.2

```
          201                                                    250
Adhesin   REAWYAYSKK NSTKGL...K MIDVSSEQDP AKISALFNKK DTAIQSSYNK
   LapT   VPVLAEMARK HEGLDFVGEK INNPNYFGDG LGIATHL..K NQVLVDQFNA
   Peb1   KSIL...... ...LGYVDDK SEILPDSFEP QSYGIVTKKD DPAFAKYVDD
              :     :K : : G:   K : : *   DP  I:*:: KK D A: * :N 251             275
Adhesin   ALKELQQDGT VKKLSEKYFG ADITE
   LapT   ALKTIKENGE YQKIYDKWMG GK...
   Peb1   FVKE..HKNE IDALAKKWGL .....
          ALKEI:::G* :*KL :K::G
```

Fig-5.1

```
             1                                                      50
    HisJ     ......MKKL ALSLSLVLAF SSATAAFAAI PQK.IRIGTD PTYAPFESKN
     LAO     ......MKKT VLALSLLIGL GATAASYAAL PQT.VRIGTD TTYAPFSSKD
  Atunop     MKFFNLNALA AVVTGVLLAA GPTQ...AKD YKS.ITIATE GSYAPYNFKD
  Atuoct     .....MKLKT ILCAALLLVA GQAA...AQE .KS.ITIATE GGYAPWNFSG
    GlnH     .......MKS VLKVSLAALT LAFAVSSHAA DKK.LVVATD TAFVPFEFKQ
 Adhesin     .......... ...AGITSVS AASAVNSELV HKGELTIGLE GTYSPYSYRK
                                        K    LTIG E  GTY:PYS *
             51                                                    100
    HisJ     AQGELVGFDI DLAKELCKRI NTQCTFVENP LDALIPSLKA KKIDAIMSSL
     LAO     AKGEFIGFDI DLGNEMCKRM QVKCTWVASD FDALIPSLKA KKIDAIISSL
  Atunop     AGGKLIGFDI DLGNDLCKRM NIECKFVEQA WVGIIPSLTA GRYDAIMAAM
  Atuoct     PGGKLDGFEI DLANALCEKM KAKCQIVAQN WDGIMPSLTG KKYDAIMAAM
    GlnH     .GDKYVGFDV DLWAAIAKEL KLDYELKPMD FSGIIPALQT KNVDLALAGI
 Adhesin     .NNKLTGFEV DLGKAVAKKM GLKANFVPTK WDSLIAGLGS GKFDVVMNNI
                KL GFEV DLGKA:AKKM LK**FVP    WD:LI::L*: GK:D::M  I
             101                                                   150
    HisJ     SITEKRQQEI AFTDKLYA.. ......ADSR LV........ .......VAK
     LAO     SITDKRQQEI AFSDKLYA.. ......ADSR LI........ .......AAK
  Atunop     GIQPAREKVI AFSRPYLLTP MTFLTTADSP LLKTQVAIEN LPLDNIAPEQ
  Atuoct     SVTPKRQEVI GFSIPYAAGI NGFAVMGDSK LAEMPGLGET YSLDSQADAA
    GlnH     TITDERKKAI DFSDGYYKSG LLVMVKANNN DV........ ..........
 Adhesin     TQTPERAKQY NFSTPYIKSR FALIVPTDSN I......... ..........
              T TPER K: :FS PY KS  :  ::V DSN :
             151                                                   200
    HisJ     NSDIQPTVAS LKGKRVGVLQ GTTQETFGNE HWAPKGIEIV SYQGQDNIYS
     LAO     GSPVQPTLES LKGKHVGVLQ GSTQEAYAND NWRTKGVDVV AYANQDLIYS
  Atunop     KAELDKFTKI FEGVKFGVQA GTSHEAFM.K QMMP.SVQIS TYDTIDNVVM
  Atuoct     KKAIADISSF LNGTTVGVQG STTASTFLDK YFKG.SVDIK EYKSVEEHNL
    GlnH     .....KSVKD LDGKVVAVKS GTGSVDYAKA NIKTK..DLR QFPNIDNAYM
 Adhesin     .....KSLKN IKGKKI.IAG TGTNNANVVK KYKGNLTPNG DFASS....L
                 KSLK  :KGKK: :  G ::T A   K  :KG       FAS       L
```

Fig-5.2

```
           201                                                              251
   HisJ    DLTA.GRIDAA  FQDEVAASEG  FLKQPVGKDY  KFGGPAVKDE  KLFGVGTGMG
    LAO    DLTA.GRLDAA  LQDEVAASEG  FLKQPAGKEY  AFAGPSVKDK  KYFGDGTGVG
 Atunop    DLKA.GRIDAS  L.ASVSFLKP  LTDKPDNKDL  KMFGPRMTGG  .LFGKGVGVG
  Atuoct   DLTS.GRLDAV  L.ANATVLAA  AIEKPEMKGA  KLVGPLFSGG  .EFG.VVAVG
   GlnH    ELGTN.RADAV  LHDTPNILY.  FIKTAGNGQF  KAVGDSLEAQ  QY.....GIA
Adhesin    DMIKQGRA.AG  TINSREAWYA  YSKKNSTKGL  KMIDVSSEQD  ...PAKISAL
           D:   GRA A:    :S  A:YA : KK    KGL KM:: S E::       *   ::
           252                                           291
   HisJ    LRKEDNELRE  ALNKAFAEMR  ADGTYEKLAK  KYFDFDVYGG.
    LAO    LRKDDTELKA  AFDKALTELR  QDGTYDKMAK  KYFDFNVYGD.
 Atunop    IRKEDADLKA  LFDKAIDAAI  ADGTVQKLSQ  QWFGYDASPKQ
  Atuoct   LRKEDTALKA  DFDAAIKAAS  EDGTIKTLSL  KWFKVDVTPQ.
   GlnH    FPKGSDELRD  KVNGALKTLR  ENGTYNEIYK  KWFGTEPK...
Adhesin    FNKKDTAIQS  SYNKALKELQ  QDGTVKKLSE  KYFGADITE.
           F K*DTA::*  *:NKALKEL:  QDGTVKKLS   KYFG D:T
```

Fig-6.1

```
            1                                                                    50
Mtu85c     MTFFEQVRRL  RSAATTLPRR  VAIAAMGAVL  VYGLVGTFGG  PATAGAFSRP
Mlep85c    MKFLQQMRKL  FGLAAKFPAR  LTIAVIGTAL  LAGLVGVVGD  TAIAVAFSKP
Mtu85b     ..MTDVSRKI  RA....WGRR  LMIGTAAAVV  LPGLVGLAGG  AATAGAFSRP
Mlep85b    ..MIDVSGKI  RA....WGRW  LLVGAAAT..  LPSLISLAGG  AATASAFSRP
Mlep85a    ..........  ..........  ..........  ..........  ..........
Adhesin    ..........  ..........  ..........  .AGSTSVSAA  SAVNSELVHK
                                              :G *::*::   *A:*:*::**

51                                                                  100
Mtu85c     G.LPVEYLQV  PSA.SMGRDI  KV.QFQGGGP  ..HAVYLLDG  LRAQDDY..N
Mlep85c    G.LPVEYLQV  PSP.SMGHDI  KI.QFQGGGQ  ..HAVYLLDG  LRAQEDY..N
Mtu85b     G.LPVEYLQV  PSP.SMGRDI  KV.QFQSGGN  NSPAVYLLDG  LRAQDDY..N
Mlep85b    G.LPVEYLQV  PSE.AMGRTI  KV.QFQNGGN  GSPAVYLLDG  LRAQDDY..N
Mlep85a    ..........  ..........  ..........  ..........  ..........
Adhesin    GELTIG.LET  YSPYSYRKNN  KLTGFEVDGK  ...AVAKKMG  LKA..NFVPT
           G L*::  L:*  Sp S   ::  K: *F: :G*    AV        G L:A  ::   *

101                                                                 150
Mtu85c     GWDINTPAFE  EYYQSG.LSV  IMPVGGQSSF  YTDWYQPSQS  NGQNYTYKWE
Mlep85c    GWDINTPAFE  EYYHSG.LSV  IMPVGGQSSF  YSNWYQPSQG  NGQHYTYKWE
Mtu85b     GWDINTPAFE  WYYQSG.LSI  VMPVGGQSSF  YSDWYSPACG  KAGCQTYKWE
Mlep85b    GWDINTSAFE  WYYQSG.LSV  VMPVGGQSSF  YSDWYSPACG  KAGCTTYKWE
Mlep85a    ..........  ..........  ..........  ..........  ..........
Adhesin    KWSL.IAGLG  ....SGKFDV  VM........  .NNITTPERA  KQ....YNFS
           W*:  *::::       SG :*V  VM             *N  *P**:  K*    Y*:*

151                                                                 200
Mtu85c     T.FLTREMPA  WLQANKGVSP  TGNAAVGL..  ....SMSGGS  ...ALILAAY
Mlep85c    T.FLTQEMPS  WLQANKNVLP  TGNAAVGL..  ....SMSGSS  ...ALILASY
Mtu85b     T.FLTSELPQ  WLSANRAVKP  TGSAAIGL..  ....SMAGSS  ...AMILAAY
Mlep85b    T.FLTSELPK  WLSANRSVKS  TGSAVVGL..  ....SMAGSS  ...ALILAAY
Mlep85a    ...LTSELPQ  YLQSNKQIKP  TGSAAVGL..  ....SMAGLS  ...ALTLAIY
Adhesin    TPYIKS...R  FL.....IVP  TDSNIKSLKN  IKGKKIAGTG  TNNANVVKKY
           T ::*S    * :L      ::P  T:S*: :L      *:AG*:      A ::  Y
```

Fig-6.2

```
           201                                                          250
Mtu85c    YPQQFP...Y AASLSGFLNP SEGWWPTLIG LAMNDSGGYN ANSMWGPSSD
Mlep85c   YPQQFP...Y AASLSGFLNP SEGWWPTMIG LAMNDSGGYN ANSMWGPSTD
Mtu85b    HPQQFI...Y AGSLSALLDP SQGMGPSLIG LAMGDAGGYK AADMWGPSSD
Mlep85b   HPDQFI...Y AGSLSALMDS SQGIEPQLIG LAMGDAGGYK AADMWGPPND
Mlep85a   HPDQFI...Y VGSMSGLLDP SNAMGPSLIG LAMGDAGGYK AADMWGPSTD
Adhesin   K GNLPNGDF ASSL.DMIK. .QGR...... .....AAGIN SREAWY....
           * :*:P     : A:SL ::::   QG                A:G*N :*: W 251                                                          300
Mtu85c    PAWKRNDPMV QIPRLVANNT RIWVYCGNGT PSDLGGDNIP AKFLEGLTLR
Mlep85c   PAWKRNDPMV QIPRLVANNT RIWVYCGNGA PNELGGDNIP AKFLESLTLS
Mtu85b    PAWERNDPTQ QIPKLVANNT RLWVYCGNGT PNELGGANIP AEFLENFVRS
Mlep85b   PAWQRNDPIL QAGKLVANNT HLWVYCGNGT PSELGGTNVP AEFLENFVHG
Mlep85a   PAWKRNDPTV NVGTLIANNT RIWMYCGNGK PTELGGNNLP AKLLEGLVRT
Adhesin   .AYSKK.... .......NST K.....GLGI ..DVSSEQDP AK.ISAL.FN
           A:*:*              N*T :     G G*   D::::* P AK :*:L ::

301                                                          350
Mtu85c    TNQTFRDTYA ADGGRNGVFN FPPNGTHSWP ..YWNEQLVA MKADIQHVLN
Mlep85c   TNEIFQNTYA ASGGRNGVFN FPPNGTHSWP ..YWNQQLVA MKPDIQQILN
Mtu85b    SNLKFQDAYN AAGGHNAVFN FPPNGTHSWE ..YWGAQLNA MKGDLQSSL.
Mlep85b   SNLKFQDAYN GAGGHNAVFN LNADGTHSWE ..YWGAQLNA MKPDLQNTL.
Mlep85a   SNIKFQDGYN AGGGHNAVFN FPDSGTHSWE ..YWGEQLND MKPDLQQYL.
Adhesin   KDTAIQSSYN .....KALKE LQQDGVKKLS EKYFGADITE ..........
           *:* :Q:*YN      *A: : L*:DG***:*   Y:GA::**

351        364
Mtu85c    GATPPAAPAA PAA*
Mlep85c   GSNNNA*... ....
Mtu85b    GAG*...... ....
Mlep85b   MAVPRSG*.. ....
Mlep85a   GATPGA*... ....
Adhesin   .......... ....
```

ADHERENCE FACTORS OF NON PATHOGENIC MICROORGANISMS AND APPLICATIONS THEREOF FOR SCREENING MICROORGANISMS FOR SPECIFIC PROBIOTIC PROPERTIES; NOVEL PHARMACEUTICAL COMPOSITIONS AND FOOD ADDITIVES COMPRISING SUCH MICROORGANISMS AND ADHERENCE FACTORS

SUMMARY OF THE INVENTION

This invention relates to the screening of bacteria, in particular non pathogenic bacteria for those bacteria that can adhere to specific sites of the mucosa called receptors. More specifically the invention is directed at screening of non pathogenic Gram positive bacteria in particular lactic acid bacterial (LAB) species, more in particular bacteria of the genera *Lactobacillus* and *Bifidobacterium*. A preference is expressed for screening bacteria indigenous to farm animals, pets and humans.

The invention comprises a method of screening for a particular group of adherence factors of the non pathogenic bacteria not previously recognised. In particular the adherence factors e.g. of Lactobacilli are of interest. This novel group of adherence factors of non pathogenic bacteria comprises proteins that are structurally related to virulence factors of certain classes of pathogenic microorganisms.

The invention also relates to the application of bacteria obtainable via the screening method of the invention, in particular to Lactobacilli producing said adherence factors, application of the adherence factors as such, application of parts of the bacteria and application of parts of an adherence factor from the novel group for various pharmaceutical applications. Such application may comprise the treatment or prophylaxis of infections of the gastro-intestinal tract, the respiratory tract, urogenital tract, the oral cavity or any other part of the body in particular any internal part of the body that can be colonised by pathogenic microorganisms.

Another suitable example of application comprises the targeting of specific compounds to cells of the mucosa, for example with the aim to evoke a specific mucosal immune response against said compound, or to modulate the immune response.

Novel microorganisms obtainable e.g. through recombinant DNA technology expressing or overexpressing any of the novel adherence factors or effective parts thereof are also included within the invention.

The nucleic acid sequences encoding the adherence factors and fragments of said sequences encoding mucosa binding expression products are also part of the invention as are the recombinant products resulting from expression of said nucleic acid sequences.

Novel pharmaceutical compositions comprising the nucleic acid or expression products thereof or microorganisms expressing or overexpressing an adherence factor of the novel type also fall within the scope of the invention.

BACKGROUND TO THE INVENTION

Pathogenic viruses and bacteria can adhere to specific sites of the mucosa, called receptors and invade the underlying cells via these receptors, resulting in illness or even the death of the host organism. For public and animal health care it is essential that effective and cheap means are available to prevent and/or cure infections diseases in humans and animals.

The mucosa form the porte d'entrée of numerous pathogenic bacteria, for example of Gram negative bacteria of the genera Escherichia, Campylobacter, Haemophilus, Shigella, Vibrio, Pasteurella, Yersinia, Salmonella, Gram positive bacteria like Mycobacterium, Listeria, Clostridium, Staphylococcus and viruses like rotavirus, poliovirus, measles and many other microorganisms well known to a person skilled in the art of microbial infections.

Bacteria of the genus Campylobacter for example can cause severe enteritis in humans and animals after oral ingestion. *C.jejuni* is a major cause of diarrhoea in humans and occasionally in animals. Beside diarrhoea, *C.jejuni* can occasionally also cause appendicitis, meningitis, abortion and urinary tract infection in humans. In developed countries, persons of all ages are affected and Campylobacter infections are as common as infections caused by Salmonella, Shigella or *Vibrio cholerae*.

Mycobacteria such as *Mycobacterium tuberculosis* and *Mycobacterium leprae* also cause serious diseases such as tuberculosis and lepra respectively. These bacteria cause the death of many individuals in particular in the less well developed countries. These microorganisms invade the body via the mucosa of the respiratory tract.

Pathogenic microorganisms can adhere to parts of the body e.g. the gastro-intestinal tract, thereby initiating a disease. The studies of the adhesion of pathogenic microorganisms to parts of the body of a host organism have resulted in a wealth of data. From these studies it has become clear that adhesion of pathogenic bacteria can be mediated by proteins. Detailed information is available about proteins from pathogenic bacteria that bind to components of the extra cellular matrix, e.g. collagens, fibronectin or proteoglycans. Particular examples are the mycobacterial fibronectin-binding proteins, the fibronectin- and collagen-binding proteins of Streptococci and Staphylococci. specific enterobacterial fimbrial types, and surface proteins of Yersinias and the A-protein of Aeromonas (for a review, see Westerlund and Korhonen, Mol. Microbiol. 9:687–694 1993).

Information about the adhesion of Gram-positive, non pathogenic bacteria to surfaces of a host organism is more limited, in particular information regarding specific binding of mucosal receptors by non pathogenic microorganisms is scarce.

It is common knowledge that the normal human gastro-intestinal tract is colonized by a variety of non pathogenic microorganisms including bacteria of the genera Lactobacillus, Streptococcus, Enterococcus, Bifidobacterium, Clostridium, Bacteroides, and others. These microorganisms form part of the indigenous microflora of the human being. As such considerable interest has been directed to elucidating the mechanisms of adherence and the role of adhesion in gastro-intestinal colonisation. However the mechanisms of adhesion of LAB, a well examined group of non pathogenic bacteria present in gut microflora of humans and animals are in general more complex than those of the gastro-intestinal pathogens (Hasty et al. Infect. Immun. 60:2147–2152 1992).

Adhesion of non-pathogenic bacteria may be specific or aspecific. Hydrophobic and electrostatic adhesion mechanisms are involved in non-specific adhesion. Specific adhesion is characterized by a so-called "lock-and key mechanism", in which the adherence factor binds to a specific receptor. Specific adhesion is usually associated with the adhesion of microorganisms to receptors on living tissues. Adherence factors or adhesins are, in general, surface bound molecules. The adhesin can be firmly attached to the surface of the bacterium or loosely bound. The receptor is a component or structure on the surface of the cell where the bacterium will bind by an active site of the adhesin (Rutter et al, 1984 Mechanisms of adhesion in "Microbial adhesion and aggregation" Marshall. K. C. ed, pp 5–19, Springer-Verlag, Berlin).

Lactic acid bacteria, particularly Lactobacillus and Enterococcus, are examples of non pathogenic Gram-positive bacteria that play a key role in the establishment and maintenance of the microflora of the gastro-intestinal tract of man and animals. Lactobacillus species have been isolated from various regions of the human gastro-intestinal tract (Molin et al, J. Appl. Bacteriol. 74, 314–323 1993).

The determinants supposedly responsible for the adhesion of some strains have been studied, and certain structures are reported to be involved in the mechanism of adhesion. However, because of the complexity of the intestinal ecosystem, little is known about why and how certain bacterial strains adhere to and colonize specific regions of the gastro-intestinal tract.

There is indeed great confusion in the literature about the mechanisms of adhesion of Lactobacilli to the gastro-intestinal mucosa. Fuller described the adhesion of Lactobacillus to chicken crop epithelium and concluded that the adhesion was mediated by polysaccharides (Fuller, J. Gen Microbiol. 87:245–250 1975). However, Conway and Adams (J. Gen. Microbiol. 135:1167–1173 1989), who found no evidence for a role of polysaccharides in the adhesion of lactobacilli, suggested that other components may be involved. Other researchers have indeed shown that lipotheichoic acids (LTA) are very important in the adhesion of Lactobacillus and Streptococcus and proposed that LTA is responsible for the association of Streptococci with fibronectin and dental plaque (Hogg and Manning. J. Appl. Bacteriol. 65:483–489; Vickerman and Jones, Infect. Immun. 60:400104008 1992). Suegara et al (Infect. Immun. 12:173–179) have described that proteinaceous material mediates adhesion of lactobacilli to the rat stomach epithelium.

In Current Microbiology, Vol. 28 (1994) p. 231–236 Aleljung P. et al. describe purification of 2 collagen binding proteins of *L. reuteri* NC1B 11951 which bind to collagen type I. One of 31 kD with a sequence XSNKPIIVGSK*XV. One of 29 kD with a sequence ASS*AVNSELV. The closest homology appeared to be with a trigger factor of *E. coli*. TIG position 27–33 with a relative score of 79%. It is also stated the CnBP of *L. reuteri* do not seem to be S Protein, a protein type which has been illustrated to be involved in adhesion to chicken alimentary tract. They state "now non-pathogenic indigenous gut microflora are illustrated as binding extracellular matrix binding protein". They do not however illustrate in vitro or in vivo binding to mucosa or mucin. They merely illustrate binding to a component as such which is known to be present in mucosa. No illustration of binding to such component in the form in which it is present in mucosa is provided. It is not clear whether such binding to collagen when present in mucosa would occur due to the fact that it is unclear where the binding site is and whether such site is available or present for binding in collagen when present in mucin or mucosa. No illustration of non-pathogenic microorganism adhesion to ECM or mucosa is provided. The article is largely speculative in nature.

Recently, Toba et al have shown that adhesion of *Lactobacillus crispatus* to the extracellular matrix is mediated by the S-layer protein (Toba et al, Appl. Environm. Microbiol. 61: 1995).

In EP 0 210 579 (with a priority date of November 1984) a preparation is described containing a protein of a Mw of 14 kD claimed to be the responsible compound for the enhancement of bacterial adhesion to squameous epithelium in mice and pigs. The preparation containing the 14 kD protein was obtained by cultivating *Lactobacillus fermentum* in a medium rich in sugars and amino acids. From EP 0 210 579 it is not clear whether the adhesion promoting factor is specific for non-pathogenic bacteria or also may enhance the adhesion of pathogens that normally do not adhere. It is also not clear from EP 0 210 579 whether or not the adhesion promoting factor enhances adhesion to specific sites (receptors) or to a-specific sites. Moreover, EP 0 210 579 does not make clear what the origin of the 14 kD protein is. It remains uncertain whether the 14 kD protein is synthesized by *L. fermentum* as such or is generated from medium components by an activity of *L. fermentum*. Thus both identity and applicability of the 14 kD protein remain obscure in the publication.

A number of later publications also suggest different proteinaceous components being involved, however offer no conclusive data.

WO 90/09398 of Conway and Kjelleberg for example describes a fraction derived from *L. crispatis* 104 of over 30 kD exhibiting anti-pathogenic activity. The fraction of over 30 kD maintains it's activity after treatment with pronase or trypsin. It is obtained by growth of *L. crispatis* in complex medium. The application also mentions that the corresponding fraction of 8000–30,000 did not exhibit anti-pathogenic activity.

The application is silent on the exact nature of the responsible component or components. It suggests also inhibiting the adhesion of pathogens to gastrointestinal epithelium of humans and animals. They also indicate in this respect that adhesion of an *E. coli* K88 strain to pig intestinal mucosa was inhibited by the high molecular weight metabolites of Lactobacilli isolated from the pig but not of lactobacilli from the mouse digestive tract. Subsequent studies indicated that this was not the growth inhibiting compound in casu and the mechanism of inhibition of adhesion was to be investigated. Lactobacillus metabolites could perhaps inhibit pathogen colonisation of the mucosal surface which is a prerequisite for pathogenicity for many strains. Consequently factors in addition to growth inhibition activities should also be considered. No illustration is given of mucosal binding inhibition. What is illustrated is that *Lactobacillus fermentum* KLD inhibited growth of *E. coli* strains. *Campilobacter jejeuni, Salonella sofia* and *Streptococcus faecium* in vitro. The supernatant derivable upon growth of the *L. fermentum* with glucose e.g. BHI medium followed by dialysis and fractionation over ultrafilters with a cut-off of MW of 10,000 and 30,000 is described as being able to elicit such effect.

The most recent publication of the aforemetioned nature being that of Blomberg L.; Henriksson A.: Conway P. (Appl. Env. Microbiol. feb. 91, p499–502) in which a protein-mediated adhesion mechanism of a *Lactobacillus fermentum* strain to mouse squamous epithelium, said protein being present in a retentate fraction of culture fluid with a MW higher than 250,000 is postulated. The publication is silent on the nature of the protein and explicitly states it had not been isolated and that the efficacy had to be verified by further experiments.

In conclusion: Although the role of proteins and the nature thereof in the adhesion of bacterial pathogens is undisputed and well documented, the role of proteins in adhesion of non-pathogenic bacteria is still at the least controversial and unclear.

Although many diseases can be treated with antibiotics or drugs, there is a general tendency to limit the use of such compounds, as more and more pathogenic organisms become resistent to antibiotics and drugs. A very promising alternative to drugs for treatment of intestinal diseases is the use of non-pathogenic bacteria with probiotic properties.

Probiotics are defined as "mono or mixed cultures of living organisms which, applied as dried cells or as a fermented product to humans or animals, beneficially affect the host by improving the properties of the indigenous microflora."

Some strains of Lactobacillus and Bifidobacterium strains, reportedly, have probiotic properties. The beneficial effects have been attributed to the lowering of the pH, a condition which reduces the proliferation of Gram-negative pathogens like *Escherichia coli*. In addition, many species of lactic acid bacteria produce oligopeptides with antimicrobial properties, called bacteriocines. These compounds are bacteriostatic or bacteriocidal for Gram-positive bacterial pathogens, like Clostridium, Listeria etc.

Some Lactobacilli have been suggested as inhibiting adhesion of pathogens in animals and in in vitro models. These inhibitory effects are usually explained by non-specific steric hindrance of the receptors for pathogens. In contrast, each pathogen has a specific intestinal receptor (Falkow et al. Ann. Rev. Cell. Biol. 8: 333–363 1992).

Lactobacilli or preparations made with Lactobacilli are thus widely used to treat intestinal and urinary tract disorders (see e.g., WO 9 516 461; RU 2 000 116; WO 9 418 997; EP 0 577 903; GB 2 261 372; WO 9 301 823; WO 0 921 475; U.S. Pat. No. 7,82, 505; CA 1 298 556; EP 0 199 535; EP 0 210 579). The beneficial effects of such preparations have been attributed to various factors, but the properties and mode of action of such health stimulating compounds have either not been disclosed or are at most mere postulations. Answers regarding the mechanist of probiotics are crucial in order to find novel enhanced probiotics and optimise their use.

Considering the economic importance for food industries to use starter strains which show a scientifically proven probiotic effect, and the equally large interest of pharmaceutical companies to use GRAS (Generally Recognised As Safe) organisms as carriers for the development of mucosal vaccines, considerable effort is spent in screening bacteria, in particular GRAS organisms, more in particular Lactobacilli, for probiotic and/or immune modulating properties. A major disadvantage of the present screening programmes is that they are laborious, time-consuming and thus very costly. No easy and reliable testsystem is available to screen for probiotic or immune modulating properties of bacterial strains.

OBJECT OF THE INVENTION

The objective of the invention is to overcome the above mentioned difficulties. It is now proven unequivocally that a 29 kD proteinaceous compound is responsible for specific adhesion of *L. fermentum* to receptor sites in the mucus of pigs and mice, and thus methods to screen for other microorganisms that synthesize proteins with a similar structure and function are now provided. By demonstrating that the adherence promoting entity of *L. fermentum* is a protein of 29 kD which is structurally related to adherence factors of certain pathogenic bacteria and by demonstrating the nucleotide sequence of the gene encoding the adherence factor, the present invention provides methods for the rapid screening of microorganisms that contain a gene coding for an adhesin of the novel type and methods for screening of microorganisms that produce such an adherence factor using standard protein and nucleic acid technologies.

By demonstrating for the first time a structural relationship between virulence factors of pathogenic bacteria and adherence factors of non-pathogenic bacteria. i.e. Lactobacilli, the present invention provides methods to selectively and specifically interfere with the adhesion of pathogens to receptors on the mucosa of the gastro-intestinal tract, of the urogenital tract, of the oral cavity, of the respiratory tract and of the nasal cavity and to screen microorganisms for the capacity to interfere with adhesion of the aforementioned type of pathogens.

The many applications now possible will be explained in more detail below.

i) A more rapid and directed screening of bacteria for bacteria with probiotic properties and/or immunomodulating properties is now possible. The present invention allows rapidly screening bacteria for the capacity to interfere with the adherence of pathogens to mucosal receptors. In particular, the present invention provides a method to screen microorganisms for the presence of an adherence factor that enhances the specific adhesion of non-pathogenic Gram positive bacteria, more in particular the adhesion of lactobacilli, to bacterial receptor(s) of the mucosa of the gastro-intestinal tract, the urogenital tract, the respiratory tract and the oral/nasal cavity of humans and animals. Preferably the microorganisms to be screened will be microorganisms that are non pathogenic in humans and animals. Such microorganisms will preferably be indigenous to humans and/or animals, thus already being able to withstand the environment in which they are to be applied and also obviously not being toxic to the particular species from which they are derived. Examples of suitable non pathogenic microorganisms include bacteria of the genera Lactobacillus, Streptococcus, Enterococcus, Bifidobacterium, Clostridium and Bacteroides.

The screening can occur at protein and/or nucleic acid level using standard technologies known per se for protein detection or nucleic acid detection such as nucleic acid amplification and hybridisation techniques and protein or peptide assays using polypeptide or protein probes and/or antibodies specific for the adherence factor or factors to be detected. The present invention thus also provides a method to screen microorganisms for the presence of nucleic acid that encodes proteins with the desired adherence properties. Protein and nucleic acid assays are readily carried out by persons skilled in the art once the relevant amino acid and nucleic acid sequences have been determined as in the instant case. Such information enables probes and primers to be constructed when the nucleic acid sequence and/or the relevant amino acid sequence of the protein has been determined and isolated or synthesized as in the instant case. The isolation of the pure protein and/or expression of the pure protein enables production of antibodies in a manner known per se.

According to the invention, bacteria can be screened for the presence of a protein falling within the definition of the novel type of adherence factors of non pathogenic microorganisms as detailed below or the presence of a DNA sequence encoding such a protein or active part thereof. Application of the invention thus in particular circumvents the laborious and costly route of screening bacteria for the capacity to adhere to living tissue. More in particular, application of the invention circumvents the use of animals and/or human volunteers for screening purposes.

A method of screening non pathogenic microorganisms for a microorganism capable of specifically binding mucosa, said method comprising detection in a manner known per se of the presence of a particular protein on or in a microorganism on or in a culture of microorganisms, said particular protein being a protein as described herein falls within the scope of protection. Alternatively a method of screening non pathogenic microorganisms for a microorganism capable of specifically binding mucosa, said method comprising detection in a manner known per se of the presence of a particular gene on or in a microorganism on or in a culture of microorganisms, said particular gene encoding a protein as described herein also falls within the scope of the invention.

The invention also covers a kit suitable for detection of a non pathogenic microorganism capable of specifically binding mucosa, said kit comprising a component capable of specifically binding to a protein as described herein such as an antibody. In another embodiment the invention comprises a kit suitable for detection of a non pathogenic microorganism capable of specifically binding mucosa, said kit comprising a component capable of specifically binding to a part of a nucleic acid sequence encoding a protein as described herein such as a nucleic acid probe or primer.

ii) By applying the protein or polypeptide capable of specifically binding mucosa to a human or animal or by applying a microorganism capable of expressing such a protein or polypeptide or a culture of such a microorganism to a human or an animal it now becomes possible to interfere with the adhesion of pathogenic microorganisms to mucosa or mucin. In particular it becomes possible to prevent or reduce adhesion by pathogenic microorganisms to mucosa of the urogenital tract, gastro-intestinal tract, respiratory tract and/or oral/nasal cavity of humans and animals. Particularly interesting is that the invention offers a method to efficiently and specifically interfere with the adhesion of certain classes of pathogens to bacterial receptors of the mucosa and to screen for microorganisms capable of interfering with adhesion of certain classes of pathogens. Pathogens that may now be combatted comprise both Gram positive and Gram negative microorganisms in particular those that specifically bind mucosa receptors. Examples of pathogens to be combatted comprise strains of the genera Escherichia, Campylobacter, Haemophilus, Shigella, Vibrio, Pasteurella, Yersinia, Salmonella, Mycobacterium, Listeria, Clostridium, Staphylococcus and viruses like rotavirus, poliovirus and measles.

The invention exploits the conclusion that the infectivity of pathogens that adhere to a mucosal receptor through an adherence factor similar to that of the adhesion protein of *L. fermentum* 104R, will be reduced by probiotic bacteria harbouring an adhesion protein with a structure like that of the adhesion protein of *L. fermentum* 104R, by specific interaction with the receptor, rather than by the more general mechanism of steric hindrance.

According to the present invention, a strategy can be devised to specifically inhibit adherence of certain pathogens (those that adhere by means of an adherence factor that is stucturally related to the adhesion protein of *L. fermentum*), by administering e.g. in food or feed or as pharmaceutical composition such adhesion proteins or, microorganisms that produce such adhesion proteins. The application can be topical, oral or intravenous in any dosage form normally applied for pharmaceutical compositions and/or feed additives. The dosage form selected will depend on the type of infectious pathogen to be combatted. The dosage form may be solid or liquid. Certain standards with regard to purity and hygiene i.e. sterility normally applicable for such compositions must be adhered to. Such circumstances are well known to a person skilled in the art.

A composition comprising a component selected from the group of components comprising a protein or peptide as described herein an expression vector as described herein a recombinant microorganism as described herein or a part of said microorganism, said part expressing mucosa binding promoting activity a non pathogenic microorganism capable of expressing a protein or peptide as described herein or a part of said microorganism, said part expressing mucosa binding promoting activity as pharmaceutically active component and a pharmaceutically acceptable carrier in a pharmaceutically acceptable dosage form is covered by the invention. A composition comprising the above-mentioned components in a form suitable for use as food additive is also envisaged to fall within the scope of the invention. The use of a component selected from the group of components comprising a protein or peptide as described herein an expression vector as described herein a recombinant microorganism as described herein or a part of said microorganisn, said part expressing mucosa binding promoting activity a non pathogenic microorganism capable of expressing a protein or peptide as described herein or a part of said microorganism, said part expressing mucosa binding promoting activity as pharmaceutically active component in a pharmaceutical composition for prophylaxis and/or treatment of disease or illness associated with a mucosa colonising pathogenic microorganism also falls within the scope of the invention.

As will be apparent from the above a method for improving food products comprising addition of a product as described herein and/or a non pathogenic microorganism capable of expressing a protein or peptide as described herein or a part of said microorganism, said part expressing mucosa binding promoting activity to the food product forms an embodiment of the invention. Preferably such a method comprises addition of a product as described herein to the food product.

Obviously a food product comprising a product as described herein and/or a non pathogenic microorganism capable of expressing a protein or peptide as described herein or a part of said microorganism, said part expressing mucosa binding promoting activity as additive is also covered. A food product comprising a product as described herein as additive is a particularly suitable embodiment.

A person skilled in the art will realise that the inhibiting effect may also be obtained by addition of parts of the adherence protein, e.g. peptides derived from the 29 kD adherence protein of *L. fermentum* that are found to specifically bind to mucus and mucin. The active peptides can either be synthesized chemically or made micro-biologically by a genetically engineered microorganism. Alternatively the protein can be produced by a non recombinant or recombinant microorganism and subsequently e.g. via proteolytic digestion and optionally separation of the proteolytic fragments the desired polypeptide can be obtained. From analysis of the adhesion factor of 29 kD and the adhesion factors of the pathogenic organisms *Escherichia coli* and *Helicobacter pylori* strains and cholera toxin a consensus sequence KKXXXX (Sequence id no 30) was postulated wherein X stands for any amino acid and K stands for lysine. The 29 kD protein according to the invention comprises three such sequences. They are more or less evenly distributed over the protein molecule at positions 47–52 (KKMGLK), 173–178 (KKNSTK) and 223–238 (KKLSEK) of the mature protein. The numbering corresponds to amino acids 54–59, 180–185 and 230–235 of sequence id no. 2, of the sequence listing, in which the mature protein commences with Ala at position 8. The presence of at least one of the KKXXXK sequences, preferably two of these sequences in a protein or peptide according to the invention is preferred. Most desirably three such sequences are present. In a particular embodiment the consensus sequence will be one of the natively occurring amino acid sequences present in the 29 kD protein disclosed above. Preferably sequences corresponding to those present in their native environment will be used, such sequences can however be arrived at through genetic engineering or synthetic means generally known in the art such as through DNA synthesizers, Merrifield synthesis and cloning technology as mentioned above. Preferably such sequences will also be present in a sequence such that the tertiary structure mimics that of the native protein. This can be ascertained using computer technology in a manner known per se. Such sequences are involved in binding to negatively charged intestinal receptors.

Microorganisms that have the GRAS status, like Aspergillus, Lactobacillus and Lactococcus are well suited for such purposes. A person skilled in the art will realise that other microorganisms can also be used for production of adherence factors or peptides derived thereof. However it will be preferred for applications to humans to employ GRAS organisms. Lists of GRAS organisms are readily available to a person skilled in the field of foodstuffs and/or pharmaceuticals and are incorporated herein by reference. The US FDA for example maintains a list of such, organisms.

The conclusion that proteins like the adhesion promoting protein of L. fermentum 104R or microorganisms that produce a protein with a structure similar to that of the adhesion promoting protein of L. fermentum 104R will interfere with specific adhesion of pathogens carrying an adhesion protein with a similar structure, does not necessarily imply that such adhesion promoting proteins or adhesion promoting protein producing microorganisms will not interfere with the adhesion of pathogens that do not produce an adherence factor with a similar structure. A person skilled in the art will immediately realise that a corrolary of the use of microorganisms with an adherence promoting protein like that of L. fermentum 104R might be that adherence of such bacteria to a specific receptor will also limit the adherence of pathogens with adherence factors other than the L.fermentum-like adhesion factor, by a general mechanism of steric hindrance. Thus the pathogenic microorganisms that can be combatted do not only comprise microorganisms that bind the mucosal receptor specifically bound by the adherence factor from the non pathogenic organism.

iii) As the group of proteins exhibiting the desired activity is now known and amino acid sequences and nucleic acid sequences have been determined it is now possible to develop and/or select microorganisms capable of improved production i.e. overexpression of the desired protein or polypeptide. This can be achieved via normal optimalisation of cultivation conditions, via selection of strains expressing proteins with improved receptor binding properties in a manner known per se.

It is also possible via genetic engineering to incorporate the nucleic acid sequence or nucleic acid sequences in microorganisms of choice that thus become capable of (over)expression and preferably also secretion of mucosa binding promoting component. Preferably the microorganism will be a GRAS organism such as a lactic acid bacterium. It is also possible to incorporate the encoding sequences or sequences such that they are operably linked to regulating sequences that enable higher expression than with the regulating sequence normally associated with the encoding sequence. A number of high expression vectors are known for various microorganisms in particular GRAS microorganisms such as lactic acid bacteria. Recombinant microorganisms capable of expressing or overexpressing the polypeptide or protein capable of promoting the binding of mucosa of the novel group of adherence factors from non pathogenic microorganisms or recombinant expression vectors comprising the appropriate nucleic acid also fall within the scope of the invention. The microorganism that is genetically engineered may already express the adherence factor but the microorganism may also be selected from a group that does not natively express an adherence protein of the novel group. The microorganism may simply be used as production plant for the protein or polypeptide which may subsequently be isolated and applied as pharmaceutical or as food/feed additive, or the microorganism itself may be used as pharmaceutical or as food/feed additive. Preferably the protein or polypeptide producing microorganism will be non pathogenic. In particular GRAS microorganisms are preferred in order to enable applications of the expression product and/or microorganisms as active component of a pharmaceutical composition or food/feed additive.

The nucleic acid sequences may be incorporated onto a plasmid vector or integrated into the chromosome in any embodiment known per se in the recombinant DNA technology field. A large number of transformation and expression vectors and technologies are known in the state of the art and are currently also commercially available. Preferred are food-grade transformation and expression vectors and methods of transformation suitable for GRAS microorganisms.

Preferably the microorganisms to be selected and/or transformed have the following characteristics:

Survival of the environmental conditions at the location where it must be active Proliferation and/or colonisation at the location where it is active No immune reaction against the probiotic strain No pathogenic, toxic, allergic, mutagenic or carcinogenic reaction by the probiotic strain itself, its fermentation products or its cell components after decease of the bacteria Genetically stable, no plasmid transfer Easy and reproducible production Viable during processing and storage In general terms a recombinant microorganism is claimed comprising a nucleic acid sequence as described herein and/or an expression vector as described herein, said nucleic acid sequence and/or expression vector being absent or in the alternative being present in a lower copy number or being expressed to a lower degree in the corresponding non recombinant microorganism. In a further embodiment the invention comprises a recombinant microorganism as just defined, said microorganism being a non pathogenic microorganism, preferably indigenous to the microflora of a human or animal, more preferably to the microflora of a human.

The invention also encompasses a nucleic acid sequence encoding any of the proteins or peptides as described and an expression vector comprising such a nucleic acid sequence, operably linked to an expression regulating sequence, said expression vector being capable of expressing the nucleic acid in a non pathogenic microorganism such as a GRAS microorganism and said expression vector preferably comprising nucleic acid derived from a GRAS microorganism. In a further embodiment the expression vector according to the invention is a vector, wherein the expression regulating sequences are not naturally associated with the gene encoding the adherence factor from which the nucleic acid sequence is derived.

iv) As the 3D structure, amino acid sequence and nucleic acid sequence of an adherence protein have now been ascertained and the similarity between other protein groups has been determined it lies within reach of a person skilled in the art to design a protein or polypeptide exhibiting improved binding characteristics and thus improved results in pharmaceutical applications or as food/feed additive. The invention thus also covers mutant polypeptides and proteins exhibiting better mucosa binding than the protein with amino acid sequences of FIG. 3 and better mucosa binding activity than any of polypeptides I–V as defined in the experimental part of the subject description. The invention also comprises equivalent sequences as available in nature and as mutants i.e. nucleic acid sequences encoding protein or polypeptide having at least the mucosa binding activity of the 29 kD protein and such proteins or polypeptides as well as their application in any of the methods of the description and/or claims.

v) Having discovered a group of proteins and peptides capable of specifically binding mucosa it also becomes possible not only to target the microorganism expressing the protein or peptide to mucosa but also to use such microorganism as carrier for targeting additional compounds such as drugs, immunomodulators or antigens for eliciting an immune reponse to the mucosa. The microorganism may be selected for already having this particular characteristic or may be genetically engineered so that it subsequently produces the desired drug, immunomodulator or antigen. It also becomes possible to develop fusion proteins or peptides comprising the mucosa binding promoting amino acid sequences and additional desired amino acid sequences or molecules with the characteristic activity of choice that has to be targeted to the mucosa. A whole line of new pharmaceutical compounds specifically targeted to the mucosa can thus be developed. The invention covers such novel microorganisms and molecules and applications thereof as pharmaceutical compositions. The invention thus also covers a method for targeting a bacterium that expresses a gene of interest, for example a gene encoding an antigen of a pathogenic organism, to specific receptors of the mucosa, thereby evoking a specific immune response against the antigen and/or modulating an immune reponse. The invention covers a fusion protein or peptide comprising a protein or peptide as described herein attached to a drug, immunomodulator or antigen of choice.

Use of a component selected from the group of components comprising
  a protein or peptide as described herein
  an expression vector as described herein
  a recombinant microorganism as described herein or a part of said microorganism, said part expressing mucosa binding promoting activity
  a non pathogenic microorganism capable of expressing a protein or peptide as described herein or a part of said microorganism, said part expressing mucosa binding promoting activity as targeting component in a pharmaceutical composition for targeting an additional pharmaceutically active component to mucosa, said additional pharmaceutical component being physically linked to the targeting component falls within the scope of the invention.

The enhancement of specific adhesion of lactobacilli to receptors of the mucosa, according to the invention, providing the opportunity to specifically target bacteria carrying compounds of interest, for example lactobacilli expressing an antigen of a pathogenic organism or a human protein, to the cells of the mucosa, thereby modulating the immune response against the antigen/human protein is a preferred embodiment of the invention.

According to the invention, the adhesion capacity of probiotic strains may be modulated by altering the properties of the adhesion protein. Such properties may involve interaction of the adhesion protein with the mucosal receptor or interaction with other (accessory) proteins.

DETAILED DESCRIPTION OF THE INVENTION

According to the invention, use is made in particular or a protein with a Mw of 29 kD of *L. fermentum* 104R, a strain isolated from the porcine gastrointestinal tract and/or of the DNA sequence encoding this adhesion protein, which had not been described sofar. The novel protein has adhesion promoting activities. In particular the adhesion promoting activity comprises exhibiting binding to mucosa or mucin. The adhesion protein is present on the surface and is also shed off into the culture medium by *L. fermentum* 104R.

The invention more in particular exploits a special property of the adhesion promoting protein, namely that it is structurally similar to virulence proteins of several pathogenic bacteria, e.g. to adherence factors from *Campylobacter jejuni, Pasteurella haemolytica* and Mycobacterium. These features are documented in the following paragraph. According to the invention the presence of proteins with properties similar to those of the 29 kD protein can be determined using the Western blot technique, a technique well known to persons skilled in the art.

The adhesion promoting protein from *L. fermentum* 104R belongs to a class of proteins, called Class III solute transporters, of which the histidine transporter (HisJ), glutamine transporter (GlnH) and the lysine, arginine and ornithine transporter (LAO) of Enterobacteriaceae are the prototypes The 3-D structure of two of these proteins, HisJ and LAO is known. The amino acid sequence of the adhesion promoting protein of *L. fermentum* 104R shows a striking similarity with on the one hand adherence proteins of pathogens, Peb1 of *C. jejuni* and LapT of *P. haemolytica*, and on the other hand with members of Class III solute transporter proteins, like LAO and HisJ. Protein modelling has shown that the predicted 3-D structure of the *L. fermentum* adhesin is also similar to that of LAO and HisJ. Amino acids in proteins in domain I of Class III solute transporters that are essential for ligand binding are conserved among all members of this class of proteins. These amino acids were also found at similar positions in the adhesion promoting proteins of *L. fermentum* 104R and in the virulence protein of *C. jejuni*. In other words, the adhesion promoting protein from *L. fermentum* 104R has a 3-D structure which is similar to that of adherence factors of pathogens like *C. jejuni* and *P. haemolytica*.

A protein belonging to the group of novel proteins as defined according to the invention is defined as a protein obtainable from a non pathogenic microorganism, said protein having mucosa binding promoting activity and a molecular weight of 20–40 kD. Preferably the weight lies between 20–30 kD. Specific embodiments are disclosed herein. In particular a protein according to the invention comprises one or more of the following properties:
 a) a molecular weight between 20 and 40 kD
 b) an amino acid sequence exhibiting more than 20% identical amino acids and more than 40% similar amino acids with the amino acid sequence of class III solute transporters and/or virulence proteins Peb1 of *C. jejuni,* LapT of *P. haemolytica* and *Mycobacterium tuberculosis* or *Mycobacterium leprae* 85K complex proteins A, B and C
 c) promotes the specific binding to bucosal receptors also used by any of *C jejuni, P. haemolytica* or Mycobacterium d) has a 3D structure with 2 lobes like LAO or HisJ e) comprises one or more amino acid sequences that are 90% or more similar to the following amino acid sequences

I) AASAVNSELVHK (SEQ ID NO: 21)

II) ANFVPTK (SEQ ID NO: 22)

III) DTAIQSSYNK (SEQ ID NO: 23)

IV) ISALFNK (SEQ ID NO: 24)

V) IAGTGTNNA (SEQ ID NO: 25), preferably of the amino acid sequences II–V.

A specific embodiment is formed by the group of proteins further characterised in thaw the protein exhibits the consensus sequence illustrated in FIGS. 4 and 5. The proteins claimed as such do not comprise virulence factors of pathogenic microorganisms or Class III transporters, neither does the class of recombinant proteins comprise recombinant virulence factors or recombinant Class III reporters that could perhaps form state of the art at the filing date of the subject patent application.

Preferably a protein belonging to the group of proteins suitable for application according to the invention will exhibit minding promoting activity for mucosal receptors used by any of *C jejuni, P. haemolytica* or Mycobacterium higher or equal to that exhibited by the 29 kD protein of *L. fermentum* 104 with the amino acid sequence of FIG. 3 as can be determined by the mucosa binding assay illustrated in the Example.

Since the nucleotide structure of the adhesion promoting protein is known, non pathogenic microorganisms can also be screened for the presence off DNA sequences encoding proteins with a structure similar to that of the adhesion protein of *L. fermentum* 104R. The so called equivalent sequences which will encode a protein or polypeptide exhibiting at least the same mucosa binding activity. In particular such a nucleic acid sequence is a nucleic acid sequence encoding the amino acid sequence of FIG. 2 corresponding to that of the 29 kD protein of *L. fermentum* 104R. A nucleic acid sequence encoding the consensus amino acid sequence of the FIGS. 4 and 5 as such also falls within the scope of the invention. In particular a nucleic acid sequence encoding a protein of 20–40 kD comprising the amino acid consensus sequence and further corresponding to the sequence of the 29 kD sequence, the only difference being in the presence of one or more mutations resulting in substitution of amino acids by other similar amino acids such that the hydropathy profiles remain similar and no serious conformation change can be expected of the resulting protein or polypeptide falls within the scope of the invention. Such sequences are known as those wherein conservative exchange of amino acids has occurred in comparison to the sequence according to sequence id. no 2. Also the invention comprises any nucleic acid sequence capable of hybridising under stringent hybridisation conditions when carrying out a blot assay in a manner known per se. Such sequences thus comprise sequences encoded by nucleic acid sequences derivable from other non pathogenic microorganisms through cross hybridisation technology using oligonucleotide probes encoding parts of the amino acid sequence according to sequence id no 2, preferably probes in which the preferred codon usage of the microorganism to be screened has been taken into account in a manner known per se. Stringent hybridisation conditions as described for example in Molecular Cloning, a Laboratory Manual, Cold Spring Harbor Laboratory New York Maniatis. T. Fritsch, E. F. and Sambrook. J (1982) can be suitably applied to obtain such equivalent sequences. The cited reference also provides information regarding a number of other standard technologies mentioned elsewhere in the description and is incorporated herein by reference. In particular sequences from non pathogenic microorganisms belonging to the genera mentioned previously in the description are preferred. Also in a preferred embodiment at least one consensus sequence according to sequence id no 30 will be present. Alternatively or in addition one of the sequences of polypeptides I–V will be present. A protein or polypeptide with the amino acid sequence of the mature protein of sequence id no 2 in which amino acids have been mutated, outside the consensus sequences, having at least the mucosa binding activity of the mature protein of sequence id no 2 is also comprised within the invention. Also any sequence combining any of the above definitions is also included within the scope of the invention and forms a preferred embodiment. It is also possible that an equivalent sequence is not derivable as such from a microorganism but can be produced in an alternative manner e.g. recombinant DNA technology, PCR etc. The above embodiments are also valid for such alternative (mutant) sequences and fall within the scope of the invention. Suitably a protein or polypeptide according to the invention will be free of cell extract and other contaminating proteins. Substantial purity is preferable i.e. more than 80% pure. The purity being sufficient for application as pharmaceutical and food additive and for achieving the activity required in the applications according to the invention.

According to the present invention, bacteria may also be screened for the presence of proteins like the *L. fermentum* 104R adhesion protein, that can adhere to non-living surfaces like plastics or metal surfaces, such screening can occur as described above using oligo probes based on the amino acid sequence of the 29 kD adhesion protein. Preferably such a probe will encode a part of a consensus sequence of the FIGS. 4 and 5. In addition a suitable probe will comprise a sequence encoding the consensus sequence of sequence id no 30. The consensus sequence or the part thereof will be at least 5 contiguous amino acids long and preferably the probe will be comprised completely of consensus sequence. Use of a combination of such probes is also possible in order to obtain a sequence encoding a protein or polypeptide exhibiting as close an identity as possible to the 29 kD protein or active part thereof required for mucosa binding activity.

FURTHER DETAILS OF EMBODIMENTS OF THE INVENTION i) Production and purifitcation of adhesion protein from *Lactobacillus fermentum*

In a preferred embodiment of the present invention, the adhesion promoting protein of *L. fermentum* 104R is produced by cultivating bacteria in MRS broth or LDM medium (Conway and Kjelleberg, J. Gen. Microbiol. 135:1175–1186 1989) for 14 to 24 hours. The 29 kD adhesion protein is purified from the medium to apparent homogeneity by ammonium sulphate precipitation, gel-filtration and affinity chromatography. The adhesion promoting activity is detected in the fractions by adhesion inhibition and dot blot assays, and visualised by PAGE, SDS-PAGE and western blots using horse radish peroxidase labelled mucus or mucin. The purified protein has an estimated Mw of 29 kD, under non-denaturing conditions as well as under reducing and denaturing conditions (non gradient denaturing SDS-PAGE, using a calibration curve obtained with standard proteins, and gel-filtration chromatography, relative to the standard curve) and is sensitive to pronase, and therefore, differs from the adhesion proteins described and/or implied in EP 0 210 579 and WO 90/09398, as well as those described by Conway and Kjellenberg (J. Gen. Microbiol. 135, 1175–1186), Blomberg et al (Appl. Environm. Microbiol. 59, 34–39 1993) and Aleljung et al (Current Microbiology vol 28 (1994) p. 231–236. The proteins specifically disclosed as such in the cited references do not fall within the scope of the protection of the protein or peptide claims. The compositions specifically described as such in the cited references do not fall within the scope of protection of the composition claims. In particular application of the compositions of WO 90/09398 described specifically as such for inhibition of pathogens do not fall within the scope of the protection. Where specifically is mentioned in this paragraph this implies in the examples or following the materials and methods of the cited references. The scope of generic diclosures of such references can cover some aspects of the subject invention, which however nevertheless forms a selection invention vis a vis said reference.

The adhesion promoting protein could be extracted from the cell surface of *L. fermentum* by treatment of the bacteria with 1 M LiCl and low concentrations of lysozyme. The adhesion promoting protein, which had an affinity for both small intestine mucus and gastric mucin from pigs or mice, was released into the culture supernatant fluid after 24 h of growth.

ii) Screening of microorganisms for the presence of a *L. fermentum*-like adhesion protein In another preferred embodiment of the present invention, lactobacilli are screened for the presence of an adhesion promoting protein with properties similar to those of the adhesion promoting protein from *L. fermentum*, by separating proteins from the culture medium of an overnight culture by SDS-PAGE, and Western blotting using polyclonal antibodies raised in rabbits against purified adhesion protein of *L. fermentum* 104R.

iii) Screening of microorganisms for the presence of a *L. fermentum*-like adhesion protein encoding gene In another preferred embodiment of the present invention, DNA is isolated from microorganisms to be screened and subjected to PCR analysis, using sets of primers that are based on the nucleotide sequences of the *L. fermentum* 104R adhesion protein encoding gene. The products formed are analysed by standard molecular biological techniques as are described in handbooks (e.g. as cited elsewhere in this description) or commercially available kits.

iv) Synthesis of adhesion promoting protein in organisms other than *L. fermentum* 104R In another specific embodiment of the present invention, the gene encoding the adhesion protein from *L. fermentum* 104R or from another selected strain, isolated by the aforementioned procedure, is cloned behind a strong, preferably inducible promoter and secretion signal encoding sequence, in a GRAS production organism like *Aspergillus niger*, Lactobacillus etc. The culture medium is either used as such and used as food/feed additive or pharmaceutical composition, or the adhesion promoting protein is first purified (by standard techniques) and then added to food/feed preparations or pharmaceutical compositions. The nucleic acid sequence may be adjusted such that it encodes the identical amino acid sequence of the 29 kD *L. fermentum* 104R adherence protein of FIG. 2 but has codons adjusted to the preferred codon usage of the host in which it is incorporated. Details of preferred codon usage are available from sources known to a person skilled in the art of nucleic acid expression.

v) Production of peptides with adhesion promoting properties

In another preferred embodiment of the present invention, peptides derived from the *L. fermentum* 104R adhesion protein that show adhesion promoting properties are synthesized chemically and used as food/feed additive. Alternatively, DNA sequences, coding for such peptides are cloned behind a strong, preferably inducible promoter in a GRAS production organism like *A. niger* or Lactobacillus etc. In cases where the peptide encoding sequences are cloned behind a secretion signal encoding sequence and the peptides are secreted into the medium, the medium can be used as food/feed additive. In cases where the peptides are not secreted into the medium, the entire organisms, or extracts made from such organisms, can be used as food/feed additive. Alternatively the desired proteins or polypeptides may be isolated e.g. using chromotagraphy in a manner known per se for isolating protein or polypeptide e.g. in combination with antibodies specific for the protein or polypeptide to be isolated. An antibody or antibody fragment capable of binding an epitope or protein or peptide within the scope of the invention. Such an antibody may be a polyclonal antibody (see Example) or a monoclonal antibody. An antibody specifically disclosed in any of the above cited references is excluded from the scope of protection for antibody claims as such.

vi) Targeting of an antigen or human protein to mucosa

In another embodiment of the present invention, the ability of adhesion protein to specifically adhere to mucosal tissue is exploited to target an antigen of a pathogen to the mucosa to enhance a mucosal immune response against the antigen. For this purpose, microorganisms are constructed that are capable of synthesizing the adhesion protein and the antigen of interest. Alternatively, to modulate the immune response against human proteins for the sake of suppressing auto-immune responses, microorganisms carrying a gene encoding a human protein are genetically engineered in such a way that they synthesize an adhesion protein with properties similar to those of the L. fermentum adhesion protein.

EXAMPLES i) Purification and characterization of a surface protein from Lactobacillus fermentum that binds to small intestine mucus and gastric mucin from pig Spent culture fluids from 14 or 24 hour cultures were collected by centrifuging at 6000 g for 20 min and dialysing at 4° C. against ultra pure water. The retenate was concentrated by ultra filtration through a 14 KDa molecular weight cut off membrane. The high molecular weight fraction was freeze dried and stored at 4° C. Spent culture fluid was also concentrated 10 times by hollow fibre ultrafilter and ammonium sulphate was dissolved in the concentrate (40, 60 and 100% of saturation at 4° C.). The precipitates were collected by centrifugation (18000×g/30 min). dissolved in ultra pure water and dialysed against 0.01M ammonium bicarbonate. The solutions were freeze dried and kept at 4° C.

The freeze dried preparation from 24 hours spent culture fluid concentrated by ultra filtration was dissolved in HEPES-Hanks and filtered (0.22 μm) to remove insoluble particles. A 4 ml aliquot of the solution (2.1 mg of protein) was applied to a Sephadex G 200 in XK-26 column (Pharmacia-LKB, Uppsala Sweden) for gel filtration chromatography. HEPES-Hanks buffer was used to equilibrate the column and elute the sample. The fractions in each 280 nm-absorbing peak were assayed for the capacity to bind HRP-mucin and HRP-crude mucus by dot blot assay and in the inhibition of lactobacilli binding to crude mucus in microtiter plates adhesion inhibition assay. The active fractions in each 280 nm absorbing peak were pooled, dialysed and freeze dried for SDS-PAGE and western blot analysis.
Alternative purification Mucin was covalently coupled to Activated CH-sepharose 4B according to the instructions of the manufacturer (Pharmacia-LKB, Biotechnology). A column C10/40 (30 ml bed volume) was packed with this adsorbent and equilibrated with HEPES-Hanks. L. fermentum spent culture fluid, cell extracts, or active fractions from Gel filtration chromatography were loaded throw the column. Column was washed with two bed volumes of equilibrating buffer, then successively washed with different solutions (0.1 M glycine pH 3, 0.1M tris pH 8 and 0–2 M gradient of sodium chloride) at flow rates of 6 ml h$^{-1}$.

The adhesion promoting activity was detected in the fractions by adhesion inhibition and dot blot assays, and was visualized by PAGE, SDS-PAGE and western blots using horse radish peroxidase labelled mucus or mucin. The adhesion promoting protein could be extracted from the cell surface of L. fermentum by treatment of the bacteria with 1 M LiCl and low concentrations of lysozyme. The adhesion promoting protein, which had an affinity for both small intestine mucus and gastric mucin, was released into the culture supernatant fluid after 24 h of growth. The active fraction was characterized by assessing the presence of carbohydrates in (periodic-acid Schiff stain procedure, SIGMA, and DIG glycan detection kit, Boehringer Mannheim, Germany) and the heat sensitivity of the active region of the adhesion promoting protein. The adhesion promoting activity lacked carbohydrates and remained completely biologially active, when LiCl cell extracts from L. fermentum were heated for 5 min at 100° C. and tested by dot blot adhesion assay.

The purified protein has an estimated Mw of 29 kD, under non-denaturing conditions as well as under reducing and denaturing conditions (SDS-PAGE, using a calibration curve obtained with standard proteins, and gel-filtration chromatography, relative to the standard curve: FIG. 1).

The adhesion promoting protein was further characterized by determination of the N-terminal amino acid sequence, showing the following sequence:

AXXAVNXELV(V)(K)

When the adhesion promoting protein was digested with modified porcine trypsin and the peptides formed were purified by reverse-phase HPLC, a number of peptides were found to specifically adhere to mucus and mucin, as measured by dot blot and mucin adhesion assays. The aminoacid sequence of the peptides are: I:ANFVPTK, II:DTAIQSSYNK, III:ISALFNK, IV:IIAG(T)G(T)NNA. In these sequences X most likely represents serine (S).

ii) Cloning and sequencing of adherence factor encoding protein

The adhesion promoting protein gene was cloned from a genomic bank of L. fermentum 104R. To generate a probe with which adhesion gene sequences could be identified, oligonucleotide primers were synthesized, based on the aminoacid sequence data of the sequenced peptides of the adhesion promoting protein. These oligonucleotides were used in various combinations in PCR reaction. Oligonucleotides 42 (sense: 5'-CTI.GCI.GTI.AAC/T.TCI.GAG/A.TTG/A.GT-3') and 105 (antisense: 5'-GCC.GGGA.TCC.TTT.G/A/T/CGT.G/TGG.G/TAC.G/AAA.G/ATT.G/A/TGC-3') corresponding to the N terminal peptide and peptide I, respectively, yielded a PCR product of 183 bp flanked by EcoRI and BamHI sites, which hybridized in a Southern blot with a 3.5 kb SstI-PstI chromosomal L. fermentum fragment. The fragment was cloned in pGEM3 in E. coli. The position of the adhesion encoding gene was determined by restriction enzyme analysis and the nucleotide sequence of the relevant part of the 3.5 kb fragment was determined (FIG. 2). The predicted aminoacid sequence of the adhesion protein is given in FIG. 3.

iii) Analysis of the aminoacid sequence of the L. fermentum 104R adhesion protein Computer assisted analysis of the aminoacid sequence of the L. fermentum 104R adhesion protein was carried out. FIG. 4 shows that the protein shows striking similarity with the virulence proteins Peb1 from C. jejuni and LapT from P. haemolytica. FIG. 5 shows that the L. fermentum adhesion protein also shows similarity with Class III solute transporters. FIG. 6 shows that the adhesion protein shows similarity to 85 K complex virulence proteins of Mycobacterium leprae and Mycobacterium tuberculosis. Protein modelling studies indicate that the predicted 3-D structure of the adhesion protein of L. ferentum 104R is similar to that of LAO and HisJ. These studies also indicate that Peb1 has a 3-D structure which is similar to that of LAO and HisJ.

iv) Determination of adhesion protein-like proteins in Lactobacillus strains

Nearly 20 Lactobacillus strains were cultivated in LDM medium, the culture medium was collected and the proteins separated by SDS-PAGE. The presence of adhesion protein-like protein was determined by Western blotting according to standard molecular biological techniques. The results, which are presented in Table 1, show that some Lactobacillus strains do produce an adhesion protein-like protein whereas others don't.

BRIEF DESCRIPTION OF THE FIGURES

FIGS. 1a—1c SDS-PAGE and Western blot of the adhesion promoting protein (APP) using HRP labelled mucus for blotting. A) Molecular weight markers (lane 1); APP after affinity chromatography (lanes 2, 6 and 7); APP from native PAGE (lanes 3, 4 and 5). B) Molecular weight markers (lane 1); APP from gel-filtration chromatography (lanes 2 and 3). Arrow in lane 3 indicates position of APP; C) Western blot of APP from SDS-PAGE after gel filtration chromatography (lane 1); after affinity chromatography (lane 2); 1M LiCl extraction of L. fermentum after 14 h of growth (lane 3); from PAGE (lane 4).

FIG. 2 Nucleotide sequence of the adhesion promoting protein of L. fermentum 104R. The open reading frame starts at nucleotide 1 and ends at nucleotide 734.

FIG. 3 Amino acid sequence of the adhesion promoting protein of L. fermentum 104R.

FIGS. 4.1–4.2 Comparison of the amino acid sequences of the adhesion promoting protein of L. fermentum 104R, Peb1 from C. jejuni and LapT from P. haemolytica. A consensus sequence is given below the sequences. Bold letters indicate identical aminoacids or conserved substitutions.

FIGS. 5.1–5.2 Comparison of the aminoacid sequences of the adhesion promoting protein of L. fermentum 104R and Class III solute transport proteins (Atunop, nopaline of Agrobacter tumefaciens; Atuoct, octopine Agrobacter tumefaciens; GlnH, glutamine binding protein of E. coli; HisJ, histidine binding protein, LAO, lysine, arginine, ornithine binding protein of Salmonella thyphimurium. A consensus sequence is given below the sequences. Aminoacids in adhesion promoting protein that also occur in other proteins are indicated in bold capital letters; colons indicate a conserved substitution and asterics a less conserved substitution.

FIG. 6 Comparison of the aminoacid sequences of the adhesion promoting protein of L. fermentum 104R and proteins of the 85K complex of Mycobacterium. A consensus sequence is given below the sequences. Aminoacids that are identical in adhesin and in one or more Mycobacterium proteins are indicated in bold capital letters. Conserved substitutions are indicated with a colon, and less conserced substitutions with an asterisc.

TABLE 1

Western blot of culture medium of Lactobacillus strains using antibodies raised against L. fermentum 104R adhesion promoting protein as a probe

| | Signal |
|---|---|
| L. gasseri NCK 89 | + |
| L. reuteri ML1 | ++ |
| L. murinus | + |
| L. fermentum 2399 | +/− |
| L. plantarum | ++ |
| L. fermentum KLD | − |
| L. animalis 364T | + |
| L. animalis 364 | +/− |
| L. casei ATCC 393 | +/− |
| L. acidophilus NCK 65 | − |
| L. animalis 362 | − |
| L. plantarum 8014 | +/− |
| L. plantarum LP80 | + |
| L. brevis R3 | + |
| L. brevis ML12 | + |
| E. coli | − |
| L. fermentum 104R | ++ |
| L. plantarum 256 | ++ |

What is claimed is:

1. An isolated and purified protein having mucosal binding activity and a molecular weight of 29 kD as measured by non-gradient denaturing SDS-PAGE, wherein said protein comprises an amino acid sequence as set forth in SED ID NO:2.

2. The protein according to claim 1, wherein a polyclonal or monoclonal antibody raised against said protein binds to said protein.

3. A fusion protein comprising a protein having mucosa binding activity according to claim 1 attached to a drug, an immunomodulator or antigen.

4. A method for screening non-pathogenic microorganisms in a culture, capable of specifically binding to mucosa, said method comprising detecting the presence of a protein according to claim 1.

5. A recombinant polypeptide comprising an amino acid sequence as set forth in SEQ ID NO:2.

6. The recombinant polypeptide according to claim 5, wherein a polyclonal or monoclonal antibody raised against said recombinant polypeptide binds to said recombinant polypeptide.

7. The recombinant polypeptide according to claim 5, consisting of SEQ ID NO. 2.

8. A fusion protein comprising a recombinant polypeptide having mucosa binding activity according to claim 5 attached to a drug, an immunomodulator or antigen.

9. A method for screening non-pathogenic microorganisms in a culture, capable of specifically binding to mucosa, said method comprising detecting the presence of a recombinant polypeptide according to claim 5.

10. An isolated and purified polypeptide comprising an amino acid sequence as set forth in SEQ ID NO: 2.

11. The polypeptide according to claim 10, wherein a polyclonal or monoclonal antibody raised against said polypeptide binds to said polypeptide.

12. A fusion protein comprising a polypeptide having mucosa binding activity according to claim 10 attached to a drug, an immunomodulator or antigen.

13. A method for screening non-pathogenic microorganisms in a culture, capable of specifically binding to mucosa, said method comprising detecting the presence of a polypeptide according to claim 10.

* * * * *

SEQUENCE LISTING

<160> NUMBER OF SEQ ID NOS: 30

<210> SEQ ID NO 1
<211> LENGTH: 747
<212> TYPE: DNA
<213> ORGANISM: Artificial Sequence
<220> FEATURE:
<223> OTHER INFORMATION: Description of Artificial Sequence:Sequence to
      adhesion promoting protein L. fermentum 104R

<400> SEQUENCE: 1

```
ctgcaggaat cacaagtgtt tctgctgctt cagctgttaa ttcagaatta gttcataagg      60
gagaattaac aattggtctt gagggaacgt actctccgta ctcttatcgt aaaaataaca     120
aattaactgg ctttgaagta gatcttggta aagcagttgc taaaagatg ggcttaaaag     180 ctaactttgt accaactaaa tgggattcgc taattgccgg tcttggttca ggtaagtttg     240
atgtagtaat gaacaacatt acacagacac ctgaacgggc caagcaatat aatttctcta     300
ccccatatat caagtcccgg tttgcattaa ttgttcctac tgatagtaac atcaaaagct     360
tgaagaatat taaaggcaag aagattattg ctggtacggg aactaataat gcgaatgtgg     420
taaaaaaata taagggtaac cttacaccaa atggcgattt tgctagttcc ttagatatga     480
tcaagcaagg tcgggctgcc gggacaatta actcccgtga agcttggtac gcttacagca     540
agaagaacag tactaagggt ctcaagatga ttgatgtttc tagtgaacaa gatccagcta     600
agatttcagc acttttaac aagaaagata ctgctattca atcttcctac aacaaggcac     660
```

```
ttaaggaact tcaacaagac ggaacagtca agaagctatc tgaaaagtac ttcggtgcag      720
atattactga ataattaaaa aagatct                                          747
```

<210> SEQ ID NO 2
<211> LENGTH: 244
<212> TYPE: PRT
<213> ORGANISM: Artificial Sequence
<220> FEATURE:
<221> NAME/KEY: UNSURE
<222> LOCATION: (244)
<223> OTHER INFORMATION: Xaa is any amino acid.
<220> FEATURE:
<223> OTHER INFORMATION: Description of Artificial Sequence:aa sequence
      adhesion promoting protein L. fermentum 104R

<400> SEQUENCE: 2

```
Ala Gly Ile Thr Ser Val Ser Ala Ala Ser Ala Val Asn Ser Glu Leu
 1               5                  10                  15

Val His Lys Gly Glu Leu Thr Ile Gly Leu Gly Thr Tyr Ser Pro
                20                  25                  30

Tyr Ser Tyr Arg Lys Asn Asn Lys Leu Thr Gly Phe Glu Val Asp Leu
                35                  40                  45

Gly Lys Ala Val Ala Lys Lys Met Gly Leu Lys Ala Asn Phe Val Pro
 50                  55                  60

Thr Lys Trp Asp Ser Leu Ile Ala Gly Leu Gly Ser Gly Lys Phe Asp
 65                  70                  75                  80

Val Val Met Asn Asn Ile Thr Gln Thr Pro Glu Arg Ala Lys Gln Tyr
                85                  90                  95

Asn Phe Ser Thr Pro Tyr Ile Lys Ser Arg Phe Ala Leu Ile Val Pro
                100                 105                 110

Thr Asp Ser Asn Ile Lys Ser Leu Lys Asn Ile Lys Gly Lys Lys Ile
                115                 120                 125

Ile Ala Gly Thr Gly Thr Asn Asn Ala Asn Val Val Lys Lys Tyr Lys
                130                 135                 140

Gly Asn Leu Thr Pro Asn Gly Asp Phe Ala Ser Ser Leu Asp Met Ile
145                 150                 155                 160

Lys Gln Gly Arg Ala Ala Gly Thr Ile Asn Ser Arg Glu Ala Trp Tyr
                165                 170                 175

Ala Tyr Ser Lys Lys Asn Ser Thr Lys Gly Leu Lys Met Ile Asp Val
                180                 185                 190

Ser Ser Glu Gln Asp Pro Ala Lys Ile Ser Ala Leu Phe Asn Lys Lys
                195                 200                 205

Asp Thr Ala Ile Gln Ser Ser Tyr Asn Lys Ala Leu Lys Glu Leu Gln
                210                 215                 220

Gln Asp Gly Thr Val Lys Lys Leu Ser Glu Lys Tyr Phe Gly Ala Asp
225                 230                 235                 240

Ile Thr Glu Xaa
```

<210> SEQ ID NO 3
<211> LENGTH: 275
<212> TYPE: PRT
<213> ORGANISM: Artificial Sequence
<220> FEATURE:
<221> NAME/KEY: UNSURE
<222> LOCATION: (1)..(18)
<223> OTHER INFORMATION: Xaa is any amino acid.
<220> FEATURE:
<221> NAME/KEY: UNSURE
<222> LOCATION: (54)
<223> OTHER INFORMATION: Xaa is any amino acid.

```
<220> FEATURE:
<221> NAME/KEY: UNSURE
<222> LOCATION: (57)
<223> OTHER INFORMATION: Xaa is any amino acid.
<220> FEATURE:
<221> NAME/KEY: UNSURE
<222> LOCATION: (77)..(79)
<223> OTHER INFORMATION: Xaa is any amino acid.
<220> FEATURE:
<221> NAME/KEY: UNSURE
<222> LOCATION: (152)..(154)
<223> OTHER INFORMATION: Xaa is any amino acid.
<220> FEATURE:
<221> NAME/KEY: UNSURE
<222> LOCATION: (170)..(172)
<223> OTHER INFORMATION: Xaa is any amino acid.
<220> FEATURE:
<221> NAME/KEY: UNSURE
<222> LOCATION: (217)..(219)
<223> OTHER INFORMATION: Xaa is any amino acid.
<220> FEATURE:
<223> OTHER INFORMATION: Description of Artificial Sequence:adhesin of
      L. fermentum 104R aligned seq3-5

<400> SEQUENCE: 3

Xaa Xaa Xaa Xaa Xaa Xaa Xaa Xaa Xaa Xaa Xaa Xaa Xaa Xaa Xaa
 1               5                   10                  15

Xaa Xaa Ala Gly Ile Thr Ser Val Ser Ala Ala Ser Ala Val Asn Ser
            20                  25                  30

Glu Leu Val His Lys Gly Glu Leu Thr Ile Gly Leu Glu Gly Thr Tyr
        35                  40                  45

Ser Pro Tyr Ser Tyr Xaa Arg Lys Xaa Asn Asn Lys Leu Thr Gly Phe
    50                  55                  60

Glu Val Asp Leu Gly Lys Ala Val Ala Lys Met Xaa Xaa Xaa Gly
 65                 70                  75                  80

Leu Lys Ala Asn Phe Val Pro Thr Lys Trp Asp Ser Leu Ile Ala Gly
                85                  90                  95

Leu Gly Ser Gly Lys Phe Asp Val Val Met Asn Asn Ile Thr Gln Thr
            100                 105                 110

Pro Glu Arg Ala Lys Gln Tyr Asn Phe Ser Thr Pro Tyr Ile Lys Ser
        115                 120                 125

Arg Phe Ala Leu Ile Val Pro Thr Asp Ser Asn Ile Lys Ser Leu Lys
130                 135                 140

Asn Ile Lys Gly Lys Lys Ile Xaa Xaa Xaa Ile Ala Gly Thr Gly Thr
145                 150                 155                 160

Asn Asn Ala Asn Val Val Lys Lys Tyr Xaa Xaa Xaa Lys Gly Asn Leu
                165                 170                 175

Thr Pro Asn Gly Asp Phe Ala Ser Ser Leu Asp Met Ile Lys Gln Gly
            180                 185                 190

Arg Ala Ala Gly Thr Ile Asn Ser Arg Glu Ala Trp Tyr Ala Tyr Ser
        195                 200                 205

Lys Lys Asn Ser Thr Lys Gly Leu Xaa Xaa Xaa Lys Met Ile Asp Val
210                 215                 220

Ser Ser Glu Gln Asp Pro Ala Lys Ile Ser Ala Leu Phe Asn Lys Lys
225                 230                 235                 240

Asp Thr Ala Ile Gln Ser Ser Tyr Asn Lys Ala Leu Lys Glu Leu Gln
                245                 250                 255

Gln Asp Gly Thr Val Lys Lys Leu Ser Glu Lys Tyr Phe Gly Ala Asp
            260                 265                 270

Ile Thr Glu
    275
```

```
<210> SEQ ID NO 4
<211> LENGTH: 275
<212> TYPE: PRT
<213> ORGANISM: Artificial Sequence
<220> FEATURE:
<221> NAME/KEY: UNSURE
<222> LOCATION: (1)..(20)
<223> OTHER INFORMATION: Xaa is any amino acid.
<220> FEATURE:
<221> NAME/KEY: UNSURE
<222> LOCATION: (57)
<223> OTHER INFORMATION: Xaa is any amino acid.
<220> FEATURE:
<221> NAME/KEY: UNSURE
<222> LOCATION: (77)..(79)
<223> OTHER INFORMATION: Xaa is any amino acid.
<220> FEATURE:
<221> NAME/KEY: UNSURE
<222> LOCATION: (147)..(149)
<223> OTHER INFORMATION: Xaa is any amion acid.
<220> FEATURE:
<221> NAME/KEY: UNSURE
<222> LOCATION: (152)..(154)
<223> OTHER INFORMATION: Xaa is any amino acid.
<220> FEATURE:
<221> NAME/KEY: UNSURE
<222> LOCATION: (170)..(172)
<223> OTHER INFORMATION: Xaa is any amino acid.
<220> FEATURE:
<221> NAME/KEY: UNSURE
<222> LOCATION: (238)..(239)
<223> OTHER INFORMATION: Xaa is any amino acid.
<220> FEATURE:
<221> NAME/KEY: UNSURE
<222> LOCATION: (273)..(275)
<223> OTHER INFORMATION: Xaa is any amino acid.
<220> FEATURE:
<223> OTHER INFORMATION: Description of Artificial Sequence:aligned
      seq3-5 of aa of LapT of P. haemolytica

<400> SEQUENCE: 4

Xaa Xaa Xaa Xaa Xaa Xaa Xaa Xaa Xaa Xaa Xaa Xaa Xaa Xaa Xaa
  1               5                  10                  15

Xaa Xaa Xaa Xaa Met Lys Lys Thr Leu Leu Thr Leu Leu Phe Gly Cys
             20                  25                  30

Val Val Thr Ala Gln Ala Gln Asp Ile Ile Val Met Glu Pro Ser Tyr
         35                  40                  45

Pro Pro Phe Glu Met Thr Glu Glu Xaa Lys Gly Glu Ile Ile Gly Phe
     50                  55                  60

Asp Val Asp Ile Ala Asn Ala Ile Cys Lys Glu Met Xaa Xaa Xaa Asn
 65                  70                  75                  80

Ala Asn Cys Thr Phe His Ser Gln Pro Phe Asp Ser Leu Ile Gln Ser
                 85                  90                  95

Leu Lys Gln Lys Gln Phe Asp Ala Ala Ile Ser Gly Met Gly Ile Thr
            100                 105                 110

Glu Pro Arg Lys Lys Gln Val Leu Phe Ser Glu Pro Tyr Phe Pro Ser
        115                 120                 125

Ser Ala Ala Phe Ile Ala Lys Lys Asp Thr Asp Phe Ala Lys Val Lys
    130                 135                 140

Thr Ile Xaa Xaa Xaa Gly Val Xaa Xaa Xaa Gln Asn Gly Thr Thr Tyr
145                 150                 155                 160

Gln His Tyr Leu Ala Lys Glu Lys Xaa Xaa Xaa Glu Tyr Asn Val
                165                 170                 175

Lys Ser Tyr Ala Ser Tyr Gln Asn Ala Ile Leu Asp Val Gln Asn Gly
            180                 185                 190
```

```
Arg Ile Asp Ala Ile Phe Gly Asp Val Pro Val Leu Ala Glu Met Ala
        195                 200                 205

Arg Lys His Glu Gly Leu Asp Phe Val Gly Glu Lys Ile Asn Asn Pro
        210                 215                 220

Asn Tyr Phe Gly Asp Gly Leu Gly Ile Ala Thr His Leu Xaa Xaa Lys
225                 230                 235                 240

Asn Gln Val Leu Val Asp Gln Phe Asn Ala Ala Leu Lys Thr Ile Lys
                245                 250                 255

Glu Asn Gly Glu Tyr Gln Lys Ile Tyr Asp Lys Trp Met Gly Gly Lys
            260                 265                 270

Xaa Xaa Xaa
        275

<210> SEQ ID NO 5
<211> LENGTH: 275
<212> TYPE: PRT
<213> ORGANISM: Artificial Sequence
<220> FEATURE:
<221> NAME/KEY: UNSURE
<222> LOCATION: (205)..(213)
<223> OTHER INFORMATION: Xaa is any amino acid.
<220> FEATURE:
<221> NAME/KEY: UNSURE
<222> LOCATION: (255)..(256)
<223> OTHER INFORMATION: Xaa is any amino acid.
<220> FEATURE:
<221> NAME/KEY: UNSURE
<222> LOCATION: (271)..(275)
<223> OTHER INFORMATION: Xaa is any amino acid.
<220> FEATURE:
<223> OTHER INFORMATION: Description of Artificial Sequence:aligned
      seq3-5 of aa sequence of Peb1 of C.jejuni

<400> SEQUENCE: 5

Met Val Phe Arg Lys Ser Leu Lys Leu Ala Val Phe Ala Leu Gly
1               5                   10                  15

Ala Cys Val Ala Phe Ser Asn Ala Asn Ala Glu Gly Lys Leu Glu
            20                  25                  30

Ser Ile Lys Ser Lys Gly Gln Leu Ile Val Gly Val Lys Asn Asp Val
        35                  40                  45

Pro His Tyr Ala Leu Leu Asp Gln Ala Thr Gly Glu Ile Lys Gly Phe
    50                  55                  60

Glu Val Asp Val Ala Lys Leu Leu Ala Lys Ser Ile Leu Gly Asp Asp
65                  70                  75                  80

Lys Lys Ile Lys Leu Val Ala Val Asn Ala Lys Thr Arg Gly Pro Leu
                85                  90                  95

Leu Asp Asn Gly Ser Val Asp Ala Val Ile Ala Thr Phe Thr Ile Thr
                100                 105                 110

Pro Glu Arg Lys Arg Ile Tyr Asn Phe Ser Glu Pro Tyr Tyr Gln Asp
        115                 120                 125

Ala Ile Gly Leu Leu Val Leu Lys Glu Lys Tyr Lys Ser Leu Ala
    130                 135                 140

Asp Met Lys Gly Ala Asn Ile Gly Val Ala Gln Ala Thr Thr Lys
145                 150                 155                 160

Lys Ala Ile Gly Glu Ala Ala Lys Ile Gly Ile Asp Val Lys Phe
                165                 170                 175

Ser Glu Phe Pro Asp Tyr Pro Ser Ile Lys Ala Ala Leu Asp Ala Lys
                180                 185                 190

Arg Val Asp Ala Phe Ser Val Asp Lys Ser Ile Leu Xaa Xaa Xaa Xaa
```

```
              195                 200                 205
Xaa Xaa Xaa Xaa Xaa Leu Gly Tyr Val Asp Asp Lys Ser Glu Ile Leu
            210                 215                 220

Pro Asp Ser Phe Glu Pro Gln Ser Tyr Gly Ile Val Thr Lys Lys Asp
225                 230                 235                 240

Asp Pro Ala Phe Ala Lys Tyr Val Asp Asp Phe Val Lys Glu Xaa Xaa
                245                 250                 255

His Lys Asn Glu Ile Asp Ala Leu Ala Lys Lys Trp Gly Leu Xaa Xaa
            260                 265                 270

Xaa Xaa Xaa
        275

<210> SEQ ID NO 6
<211> LENGTH: 275
<212> TYPE: PRT
<213> ORGANISM: Artificial Sequence
<220> FEATURE:
<223> OTHER INFORMATION: Description of Artificial Sequence:consensus
      from sel3-5 aligned aa sequences
<220> FEATURE:
<221> NAME/KEY: UNSURE
<222> LOCATION: (1)..(275)
<223> OTHER INFORMATION: Xaa is any amino acid.

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Ala Xaa Xaa Xaa Xaa Xaa Xaa Xaa
            20                  25                  30

Xaa Xaa Xaa Xaa Lys Gly Xaa Leu Xaa Ile Gly Xaa Xaa Xaa Xaa Tyr
        35                  40                  45

Xaa Pro Tyr Xaa Xaa Xaa Xaa Xaa Xaa Xaa Xaa Xaa Xaa Xaa Gly Phe
    50                  55                  60

Glu Val Asp Xaa Xaa Lys Xaa Xaa Ala Lys Xaa Met Xaa Xaa Xaa Xaa
65                  70                  75                  80

Xaa Lys Xaa Xaa Xaa Val Xaa Xaa Xaa Xaa Asp Ser Leu Ile Xaa Xaa
                85                  90                  95

Leu Xaa Xaa Gly Xaa Phe Asp Xaa Val Xaa Xaa Xaa Xaa Thr Xaa Thr
            100                 105                 110

Pro Glu Arg Xaa Lys Gln Tyr Asn Phe Ser Xaa Pro Tyr Xaa Xaa Ser
        115                 120                 125

Xaa Xaa Ala Leu Ile Val Xaa Xaa Asp Xaa Xaa Xaa Lys Ser Leu Lys
    130                 135                 140

Xaa Ile Lys Gly Xaa Xaa Ile Xaa Xaa Xaa Xaa Ala Gly Thr Xaa Xaa
145                 150                 155                 160

Xaa Xaa Xaa Xaa Xaa Xaa Xaa Lys Xaa Xaa Xaa Xaa Xaa Xaa Asn Xaa
                165                 170                 175

Xaa Xaa Xaa Xaa Asp Xaa Xaa Ser Xaa Xaa Xaa Xaa Xaa Xaa Xaa Gly
            180                 185                 190

Arg Xaa Xaa Xaa Xaa Xaa Xaa Xaa Xaa Xaa Xaa Xaa Xaa Xaa Xaa Xaa
        195                 200                 205

Xaa Lys Xaa Xaa Xaa Xaa Gly Xaa Xaa Xaa Xaa Lys Xaa Xaa Xaa Xaa
    210                 215                 220

Xaa Xaa Xaa Xaa Asp Pro Xaa Xaa Ile Xaa Xaa Xaa Xaa Xaa Lys Lys
225                 230                 235                 240

Asp Xaa Ala Xaa Xaa Xaa Xaa Asn Xaa Ala Leu Lys Glu Ile Xaa
                245                 250                 255
```

```
Xaa Xaa Gly Xaa Xaa Lys Leu Xaa Xaa Lys Xaa Xaa Gly Xaa Xaa
            260                 265                 270

Xaa Xaa Xaa
        275

<210> SEQ ID NO 7
<211> LENGTH: 292
<212> TYPE: PRT
<213> ORGANISM: Artificial Sequence
<220> FEATURE:
<223> OTHER INFORMATION: Description of Artificial Sequence:aligned aa
      sequence of HisJ with seq7-12
<220> FEATURE:
<221> NAME/KEY: UNSURE
<222> LOCATION: (1)..(292)
<223> OTHER INFORMATION: Xaa is any amino acid.

<400> SEQUENCE: 7

Xaa Xaa Xaa Xaa Xaa Xaa Met Lys Lys Leu Ala Leu Ser Leu Ser Leu
 1               5                  10                  15

Val Leu Ala Phe Ser Ser Ala Thr Ala Ala Phe Ala Ala Ile Pro Gln
            20                  25                  30

Lys Xaa Ile Arg Ile Gly Thr Asp Pro Thr Tyr Ala Pro Phe Glu Ser
        35                  40                  45

Lys Asn Ala Gln Gly Glu Leu Val Gly Phe Asp Ile Asp Leu Ala Lys
    50                  55                  60

Glu Leu Cys Lys Arg Ile Asn Thr Gln Cys Thr Phe Val Glu Asn Pro
65                  70                  75                  80

Leu Asp Ala Leu Ile Pro Ser Leu Lys Ala Lys Lys Ile Asp Ala Ile
                85                  90                  95

Met Ser Ser Leu Ser Ile Thr Glu Lys Arg Gln Gln Glu Ile Ala Phe
            100                 105                 110

Thr Asp Lys Leu Tyr Ala Xaa Xaa Xaa Xaa Xaa Xaa Xaa Xaa Ala Asp
        115                 120                 125

Ser Arg Leu Val Xaa Xaa Xaa Xaa Xaa Xaa Xaa Xaa Xaa Xaa Xaa Xaa
    130                 135                 140

Xaa Xaa Xaa Val Ala Lys Asn Ser Asp Ile Gln Pro Thr Val Ala Ser
145                 150                 155                 160

Leu Lys Gly Lys Arg Val Gly Val Leu Gln Gly Thr Thr Gln Glu Thr
                165                 170                 175

Phe Gly Asn Glu His Trp Ala Pro Lys Gly Ile Glu Ile Val Ser Tyr
            180                 185                 190

Gln Gly Gln Asp Asn Ile Tyr Ser Asp Leu Thr Ala Xaa Gly Arg Ile
        195                 200                 205

Asp Ala Ala Phe Gln Asp Glu Val Ala Ala Ser Glu Gly Phe Leu Lys
    210                 215                 220

Gln Pro Val Gly Lys Asp Tyr Lys Phe Gly Gly Pro Ala Val Lys Asp
225                 230                 235                 240

Glu Lys Leu Phe Gly Val Gly Thr Gly Met Gly Leu Arg Lys Glu Asp
                245                 250                 255

Asn Glu Leu Arg Glu Ala Leu Asn Lys Ala Phe Ala Glu Met Arg Ala
            260                 265                 270

Asp Gly Thr Tyr Glu Lys Leu Ala Lys Lys Tyr Phe Asp Phe Asp Val
        275                 280                 285

Tyr Gly Gly Xaa
        290
```

```
<210> SEQ ID NO 8
<211> LENGTH: 292
<212> TYPE: PRT
<213> ORGANISM: Artificial Sequence
<220> FEATURE:
<223> OTHER INFORMATION: Description of Artificial Sequence:aligned aa
      sequence of LA0 with seq7-12
<220> FEATURE:
<221> NAME/KEY: UNSURE
<222> LOCATION: (1)..(292)
<223> OTHER INFORMATION: Xaa is any amino acid.

<400> SEQUENCE: 8

Xaa Xaa Xaa Xaa Xaa Xaa Met Lys Lys Thr Val Leu Ala Leu Ser Leu
 1               5                  10                  15

Leu Ile Gly Leu Gly Ala Thr Ala Ala Ser Tyr Ala Ala Leu Pro Gln
                20                  25                  30

Thr Xaa Val Arg Ile Gly Thr Asp Thr Thr Tyr Ala Pro Phe Ser Ser
            35                  40                  45

Lys Asp Ala Lys Gly Glu Phe Ile Gly Phe Asp Ile Asp Leu Gly Asn
 50                  55                  60

Glu Met Cys Lys Arg Met Gln Val Lys Cys Thr Trp Val Ala Ser Asp
 65                  70                  75                  80

Phe Asp Ala Leu Ile Pro Ser Leu Lys Ala Lys Lys Ile Asp Ala Ile
                85                  90                  95

Ile Ser Ser Leu Ser Ile Thr Asp Lys Arg Gln Gln Glu Ile Ala Phe
            100                 105                 110

Ser Asp Lys Leu Tyr Ala Xaa Xaa Xaa Xaa Xaa Xaa Xaa Ala Asp
            115                 120                 125

Ser Arg Leu Ile Xaa Xaa Xaa Xaa Xaa Xaa Xaa Xaa Xaa Xaa Xaa
130                 135                 140

Xaa Xaa Xaa Ala Ala Lys Gly Ser Pro Val Gln Pro Thr Leu Glu Ser
145                 150                 155                 160

Leu Lys Gly Lys His Val Gly Val Leu Gln Gly Ser Thr Gln Glu Ala
                165                 170                 175

Tyr Ala Asn Asp Asn Trp Arg Thr Lys Gly Val Asp Val Val Ala Tyr
            180                 185                 190

Ala Asn Gln Asp Leu Ile Tyr Ser Asp Leu Thr Ala Xaa Gly Arg Leu
        195                 200                 205

Asp Ala Ala Leu Gln Asp Glu Val Ala Ala Ser Glu Gly Phe Leu Lys
    210                 215                 220

Gln Pro Ala Gly Lys Glu Tyr Ala Phe Ala Gly Pro Ser Val Lys Asp
225                 230                 235                 240

Lys Lys Tyr Phe Gly Asp Gly Thr Gly Val Gly Leu Arg Lys Asp Asp
                245                 250                 255

Thr Glu Leu Lys Ala Ala Phe Asp Lys Ala Leu Thr Glu Leu Arg Gln
            260                 265                 270

Asp Gly Thr Tyr Asp Lys Met Ala Lys Lys Tyr Phe Asp Phe Asn Val
        275                 280                 285

Tyr Gly Asp Xaa
        290

<210> SEQ ID NO 9
<211> LENGTH: 292
<212> TYPE: PRT
<213> ORGANISM: Artificial Sequence
<220> FEATURE:
<223> OTHER INFORMATION: Description of Artificial Sequence:aligned aa
``` sequence of Agrobacter tumefaciens nopaline
<220> FEATURE:
<221> NAME/KEY: UNSURE
<222> LOCATION: (25)..(27)
<223> OTHER INFORMATION: Xaa is any amino acid.
<220> FEATURE:
<221> NAME/KEY: UNSURE
<222> LOCATION: (34)
<223> OTHER INFORMATION: Xaa is any amino acid.
<220> FEATURE:
<221> NAME/KEY: UNSURE
<222> LOCATION: (179)
<223> OTHER INFORMATION: Xaa is any amino acid.
<220> FEATURE:
<221> NAME/KEY: UNSURE
<222> LOCATION: (185)
<223> OTHER INFORMATION: Xaa is any amino acid.
<220> FEATURE:
<221> NAME/KEY: UNSURE
<222> LOCATION: (205)
<223> OTHER INFORMATION: Xaa is any amino acid.
<220> FEATURE:
<221> NAME/KEY: UNSURE
<222> LOCATION: (213)
<223> OTHER INFORMATION: Xaa is any amino acid.
<220> FEATURE:
<221> NAME/KEY: UNSURE
<222> LOCATION: (242)
<223> OTHER INFORMATION: Xaa is any amino acid.

<400> SEQUENCE: 9

```
Met Lys Phe Phe Asn Leu Asn Ala Leu Ala Ala Val Val Thr Gly Val
 1               5                  10                  15

Leu Leu Ala Ala Gly Pro Thr Gln Xaa Xaa Xaa Ala Lys Asp Tyr Lys
             20                  25                  30

Ser Xaa Ile Thr Ile Ala Thr Glu Gly Ser Tyr Ala Pro Tyr Asn Phe
         35                  40                  45

Lys Asp Ala Gly Gly Lys Leu Ile Gly Phe Asp Ile Asp Leu Gly Asn
     50                  55                  60

Asp Leu Cys Lys Arg Met Asn Ile Glu Cys Lys Phe Val Glu Gln Ala
 65                  70                  75                  80

Trp Val Gly Ile Ile Pro Ser Leu Thr Ala Gly Arg Tyr Asp Ala Ile
                 85                  90                  95

Met Ala Ala Met Gly Ile Gln Pro Ala Arg Glu Lys Val Ile Ala Phe
            100                 105                 110

Ser Arg Pro Tyr Leu Leu Thr Pro Met Thr Phe Leu Thr Thr Ala Asp
        115                 120                 125

Ser Pro Leu Leu Lys Thr Gln Val Ala Ile Glu Asn Leu Pro Leu Asp
    130                 135                 140

Asn Ile Ala Pro Glu Gln Lys Ala Glu Leu Asp Lys Phe Thr Lys Ile
145                 150                 155                 160

Phe Glu Gly Val Lys Phe Gly Val Gln Ala Gly Thr Ser His Glu Ala
                165                 170                 175

Phe Met Xaa Lys Gln Met Met Pro Xaa Ser Val Gln Ile Ser Thr Tyr
            180                 185                 190

Asp Thr Ile Asp Asn Val Val Met Asp Leu Lys Ala Xaa Gly Arg Ile
        195                 200                 205

Asp Ala Ser Leu Xaa Ala Ser Val Ser Phe Leu Lys Pro Leu Thr Asp
    210                 215                 220

Lys Pro Asp Asn Lys Asp Leu Lys Met Phe Gly Pro Arg Met Thr Gly
225                 230                 235                 240

Gly Xaa Leu Phe Gly Lys Gly Val Gly Val Gly Ile Arg Lys Glu Asp
                245                 250                 255
```

```
Ala Asp Leu Lys Ala Leu Phe Asp Lys Ala Ile Asp Ala Ala Ile Ala
            260                 265                 270

Asp Gly Thr Val Gln Lys Leu Ser Gln Gln Trp Phe Gly Tyr Asp Ala
        275                 280                 285

Ser Pro Lys Gln
    290

<210> SEQ ID NO 10
<211> LENGTH: 292
<212> TYPE: PRT
<213> ORGANISM: Artificial Sequence
<220> FEATURE:
<223> OTHER INFORMATION: Description of Artificial Sequence:aligned aa
      sequence of Agrobacter tumefaciens octopine
<220> FEATURE:
<221> NAME/KEY: UNSURE
<222> LOCATION: (1)..(292)
<223> OTHER INFORMATION: Xaa is any amino acid.

<400> SEQUENCE: 10

Xaa Xaa Xaa Xaa Xaa Met Lys Leu Lys Thr Ile Leu Cys Ala Ala Leu
 1               5                  10                  15

Leu Leu Val Ala Gly Gln Ala Ala Xaa Xaa Xaa Ala Gln Glu Xaa Lys
            20                  25                  30

Ser Xaa Ile Thr Ile Ala Thr Glu Gly Gly Tyr Ala Pro Trp Asn Phe
        35                  40                  45

Ser Gly Pro Gly Gly Lys Leu Asp Gly Phe Glu Ile Asp Leu Ala Asn
    50                  55                  60

Ala Leu Cys Glu Lys Met Lys Ala Lys Cys Gln Ile Val Ala Gln Asn
65                  70                  75                  80

Trp Asp Gly Ile Met Pro Ser Leu Thr Gly Lys Lys Tyr Asp Ala Ile
                85                  90                  95

Met Ala Ala Met Ser Val Thr Pro Lys Arg Gln Glu Val Ile Gly Phe
            100                 105                 110

Ser Ile Pro Tyr Ala Ala Gly Ile Asn Gly Phe Ala Val Met Gly Asp
        115                 120                 125

Ser Lys Leu Ala Glu Met Pro Gly Leu Gly Glu Thr Tyr Ser Leu Asp
    130                 135                 140

Ser Gln Ala Asp Ala Ala Lys Lys Ala Ile Ala Asp Ile Ser Ser Phe
145                 150                 155                 160

Leu Asn Gly Thr Thr Val Gly Val Gln Gly Ser Thr Thr Ala Ser Thr
                165                 170                 175

Phe Leu Asp Lys Tyr Phe Lys Gly Xaa Ser Val Asp Ile Lys Glu Tyr
            180                 185                 190

Lys Ser Val Glu Glu His Asn Leu Asp Leu Thr Ser Xaa Gly Arg Leu
        195                 200                 205

Asp Ala Val Leu Xaa Ala Asn Ala Thr Val Leu Ala Ala Ile Glu
    210                 215                 220

Lys Pro Glu Met Lys Gly Ala Lys Leu Val Gly Pro Leu Phe Ser Gly
225                 230                 235                 240

Gly Xaa Glu Phe Gly Xaa Val Val Ala Val Gly Leu Arg Lys Glu Asp
                245                 250                 255

Thr Ala Leu Lys Ala Asp Phe Asp Ala Ala Ile Lys Ala Ala Ser Glu
            260                 265                 270

Asp Gly Thr Ile Lys Thr Leu Ser Leu Lys Trp Phe Lys Val Asp Val
        275                 280                 285
```

Thr Pro Gln Xaa
    290

<210> SEQ ID NO 11
<211> LENGTH: 292
<212> TYPE: PRT
<213> ORGANISM: Artificial Sequence
<220> FEATURE:
<223> OTHER INFORMATION: Description of Artificial Sequence:aligned aa
      sequence of E. coli GlnH
<220> FEATURE:
<221> NAME/KEY: UNSURE
<222> LOCATION: (1)..(292)
<223> OTHER INFORMATION: Xaa is any amino acid.

<400> SEQUENCE: 11

Xaa Xaa Xaa Xaa Xaa Xaa Xaa Met Lys Ser Val Leu Lys Val Ser Leu
 1               5                  10                  15

Ala Ala Leu Thr Leu Ala Phe Ala Val Ser Ser His Ala Ala Asp Lys
             20                  25                  30

Lys Xaa Leu Val Val Ala Thr Asp Thr Ala Phe Val Pro Phe Glu Phe
         35                  40                  45

Lys Gln Xaa Gly Asp Lys Tyr Val Gly Phe Asp Val Asp Leu Trp Ala
     50                  55                  60

Ala Ile Ala Lys Glu Leu Lys Leu Asp Tyr Glu Leu Lys Pro Met Asp
 65                  70                  75                  80

Phe Ser Gly Ile Ile Pro Ala Leu Gln Thr Lys Asn Val Asp Leu Ala
                 85                  90                  95

Leu Ala Gly Ile Thr Ile Thr Asp Glu Arg Lys Lys Ala Ile Asp Phe
            100                 105                 110

Ser Asp Gly Tyr Tyr Lys Ser Gly Leu Leu Val Met Val Lys Ala Asn
        115                 120                 125

Asn Asn Asp Val Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Lys Ser Val Lys Asp
145                 150                 155                 160

Leu Asp Gly Lys Val Val Ala Val Lys Ser Gly Thr Gly Ser Val Asp
                165                 170                 175

Tyr Ala Lys Ala Asn Ile Lys Thr Lys Xaa Xaa Asp Leu Arg Gln Phe
            180                 185                 190

Pro Asn Ile Asp Asn Ala Tyr Met Glu Leu Gly Thr Asn Xaa Arg Ala
        195                 200                 205

Asp Ala Val Leu His Asp Thr Pro Asn Ile Leu Tyr Xaa Phe Ile Lys
    210                 215                 220

Thr Ala Gly Asn Gly Gln Phe Lys Ala Val Gly Asp Ser Leu Glu Ala
225                 230                 235                 240

Gln Gln Tyr Xaa Xaa Xaa Xaa Xaa Gly Ile Ala Phe Pro Lys Gly Ser
                245                 250                 255

Asp Glu Leu Arg Asp Lys Val Asn Gly Ala Leu Lys Thr Leu Arg Glu
            260                 265                 270

Asn Gly Thr Tyr Asn Glu Ile Tyr Lys Lys Trp Phe Gly Thr Glu Pro
        275                 280                 285

Lys Xaa Xaa Xaa
    290

<210> SEQ ID NO 12
<211> LENGTH: 291
<212> TYPE: PRT

```
<213> ORGANISM: Artificial Sequence
<220> FEATURE:
<223> OTHER INFORMATION: Description of Artificial Sequence:aligned aa
      sequence of L fermentum 104R adhesin with seq7-12
<220> FEATURE:
<221> NAME/KEY: UNSURE
<222> LOCATION: (1)..(291)
<223> OTHER INFORMATION: Xaa is any amino acid.

<400> SEQUENCE: 12
```

Xaa Xaa Xaa Xaa Xaa Xaa Xaa Xaa Xaa Xaa Xaa Xaa Ala Gly Ile
 1               5                  10                  15

Thr Ser Val Ser Ala Ala Ser Ala Val Asn Ser Glu Leu Val His Lys
             20                  25                  30

Gly Glu Leu Thr Ile Gly Leu Glu Gly Thr Tyr Ser Pro Tyr Ser Tyr
         35                  40                  45

Arg Lys Xaa Asn Asn Lys Leu Thr Gly Phe Glu Val Asp Leu Gly Lys
         50                  55                  60

Ala Val Ala Lys Lys Met Gly Leu Lys Ala Asn Phe Val Pro Thr Lys
65                  70                  75                  80

Trp Asp Ser Leu Ile Ala Gly Leu Gly Ser Gly Lys Phe Asp Val Val
                 85                  90                  95

Met Asn Asn Ile Thr Gln Thr Pro Glu Arg Ala Lys Gln Tyr Asn Phe
            100                 105                 110

Ser Thr Pro Tyr Ile Lys Ser Arg Phe Ala Leu Ile Val Pro Thr Asp
        115                 120                 125

Ser Asn Ile Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Lys Ser Leu Lys Asn
145                 150                 155                 160

Ile Lys Gly Lys Lys Ile Xaa Ile Ala Gly Thr Gly Thr Asn Asn Ala
                165                 170                 175

Asn Val Val Lys Lys Tyr Lys Gly Asn Leu Thr Pro Asn Gly Asp Phe
            180                 185                 190

Ala Ser Ser Xaa Xaa Xaa Xaa Leu Asp Met Ile Lys Gln Gly Arg Ala
        195                 200                 205

Xaa Ala Gly Thr Ile Asn Ser Arg Glu Ala Trp Tyr Ala Tyr Ser Lys
210                 215                 220

Lys Asn Ser Thr Lys Gly Leu Lys Met Ile Asp Val Ser Ser Glu Gln
225                 230                 235                 240

Asp Xaa Xaa Xaa Pro Ala Lys Ile Ser Ala Leu Phe Asn Lys Lys Asp
                245                 250                 255

Thr Ala Ile Gln Ser Ser Tyr Asn Lys Ala Leu Lys Glu Leu Gln Gln
            260                 265                 270

Asp Gly Thr Val Lys Lys Leu Ser Glu Lys Tyr Phe Gly Ala Asp Ile
        275                 280                 285

Thr Glu Xaa
    290

```
<210> SEQ ID NO 13
<211> LENGTH: 291
<212> TYPE: PRT
<213> ORGANISM: Artificial Sequence
<220> FEATURE:
<223> OTHER INFORMATION: Description of Artificial Sequence:consensus of
      aligned aa sequences 7-12
<220> FEATURE:
<221> NAME/KEY: UNSURE
<222> LOCATION: (1)..(291)
```

<223> OTHER INFORMATION: Xaa is any amino acid.

<400> SEQUENCE: 13

```
Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Lys
             20                  25                  30

Xaa Xaa Leu Thr Ile Gly Xaa Glu Gly Thr Tyr Xaa Pro Tyr Ser Xaa
         35                  40                  45

Xaa Xaa Xaa Xaa Xaa Lys Leu Xaa Gly Phe Glu Val Asp Leu Gly Lys
         50                  55                  60

Ala Xaa Ala Lys Lys Met Xaa Leu Lys Xaa Xaa Phe Val Pro Xaa Xaa
 65                  70                  75                  80

Trp Asp Xaa Leu Ile Xaa Xaa Leu Xaa Xaa Gly Lys Xaa Asp Xaa Xaa
             85                  90                  95

Met Xaa Xaa Ile Thr Xaa Thr Pro Glu Arg Xaa Lys Xaa Xaa Xaa Phe
         100                 105                 110

Ser Xaa Pro Tyr Xaa Lys Ser Xaa Xaa Xaa Xaa Xaa Val Xaa Xaa Asp
         115                 120                 125

Ser Asn Xaa Xaa Xaa Xaa Xaa Xaa Xaa Xaa Xaa Xaa Xaa Xaa Xaa Xaa
 130                 135                 140

Xaa Xaa Xaa Xaa Xaa Xaa Xaa Xaa Xaa Xaa Xaa Lys Ser Leu Lys Xaa
145                 150                 155                 160

Xaa Lys Gly Lys Lys Xaa Xaa Xaa Xaa Gly Xaa Xaa Thr Xaa Xaa Ala
                 165                 170                 175

Xaa Xaa Xaa Lys Xaa Xaa Lys Gly Xaa Xaa Xaa Xaa Xaa Xaa Xaa Phe
             180                 185                 190

Ala Ser Xaa Xaa Xaa Xaa Xaa Leu Asp Xaa Xaa Xaa Xaa Gly Arg Ala
             195                 200                 205

Xaa Ala Xaa Xaa Xaa Xaa Ser Xaa Xaa Ala Xaa Tyr Ala Xaa Xaa Lys
         210                 215                 220

Lys Xaa Xaa Xaa Lys Gly Leu Lys Met Xaa Xaa Xaa Ser Xaa Glu Xaa
225                 230                 235                 240

Xaa Xaa Xaa Xaa Xaa Xaa Xaa Xaa Xaa Xaa Phe Xaa Lys Xaa Asp
                 245                 250                 255

Thr Ala Xaa Xaa Xaa Xaa Xaa Xaa Asn Lys Ala Leu Lys Glu Leu Xaa Gln
         260                 265                 270

Asp Gly Thr Val Lys Lys Leu Ser Xaa Lys Tyr Phe Gly Xaa Asp Xaa
         275                 280                 285

Thr Xaa Xaa
         290
```

<210> SEQ ID NO 14
<211> LENGTH: 364
<212> TYPE: PRT
<213> ORGANISM: Artificial Sequence
<220> FEATURE:
<223> OTHER INFORMATION: Description of Artificial Sequence:aligned aa
      sequence of Mycobacterium Mtu85c
<220> FEATURE:
<221> NAME/KEY: UNSURE
<222> LOCATION: (52)..(364)
<223> OTHER INFORMATION: Xaa is any amino acid.

<400> SEQUENCE: 14

```
Met Thr Phe Phe Glu Gln Val Arg Arg Leu Arg Ser Ala Ala Thr Thr
  1               5                  10                  15
```

```
Leu Pro Arg Arg Val Ala Ile Ala Ala Met Gly Ala Val Leu Val Tyr
             20                  25                  30

Gly Leu Val Gly Thr Phe Gly Pro Ala Thr Ala Gly Ala Phe Ser
         35                  40                  45

Arg Pro Gly Xaa Leu Pro Val Glu Tyr Leu Gln Val Pro Ser Ala Xaa
     50                  55                  60

Ser Met Gly Arg Asp Ile Lys Val Xaa Gln Phe Gln Gly Gly Gly Pro
 65                  70                  75                  80

Xaa Xaa His Ala Val Tyr Leu Leu Asp Gly Leu Arg Ala Gln Asp Asp
                 85                  90                  95

Tyr Xaa Xaa Asn Gly Trp Asp Ile Asn Thr Pro Ala Phe Glu Glu Tyr
            100                 105                 110

Tyr Gln Ser Gly Xaa Leu Ser Val Ile Met Pro Val Gly Gly Gln Ser
            115                 120                 125

Ser Phe Tyr Thr Asp Trp Tyr Gln Pro Ser Gln Ser Asn Gly Gln Asn
        130                 135                 140

Tyr Thr Tyr Lys Trp Glu Thr Xaa Phe Leu Thr Arg Glu Met Pro Ala
145                 150                 155                 160

Trp Leu Gln Ala Asn Lys Gly Val Ser Pro Thr Gly Asn Ala Ala Val
                165                 170                 175

Gly Leu Xaa Xaa Xaa Xaa Xaa Xaa Ser Met Ser Gly Gly Ser Xaa Xaa
            180                 185                 190

Xaa Ala Leu Ile Leu Ala Ala Tyr Tyr Pro Gln Gln Phe Pro Xaa Xaa
        195                 200                 205

Xaa Tyr Ala Ala Ser Leu Ser Gly Phe Leu Asn Pro Ser Glu Gly Trp
        210                 215                 220

Trp Pro Thr Leu Ile Gly Leu Ala Met Asn Asp Ser Gly Gly Tyr Asn
225                 230                 235                 240

Ala Asn Ser Met Trp Gly Pro Ser Ser Asp Pro Ala Trp Lys Arg Asn
                245                 250                 255

Asp Pro Met Val Gln Ile Pro Arg Leu Val Ala Asn Asn Thr Arg Ile
            260                 265                 270

Trp Val Tyr Cys Gly Asn Gly Thr Pro Ser Asp Leu Gly Gly Asp Asn
        275                 280                 285

Ile Pro Ala Lys Phe Leu Glu Gly Leu Thr Leu Arg Thr Asn Gln Thr
        290                 295                 300

Phe Arg Asp Thr Tyr Ala Ala Asp Gly Gly Arg Asn Gly Val Phe Asn
305                 310                 315                 320

Phe Pro Pro Asn Gly Thr His Ser Trp Pro Xaa Xaa Tyr Trp Asn Glu
                325                 330                 335

Gln Leu Val Ala Met Lys Ala Asp Ile Gln His Val Leu Asn Gly Ala
                340                 345                 350

Thr Pro Pro Ala Ala Pro Ala Ala Pro Ala Ala Xaa
            355                 360
```

<210> SEQ ID NO 15
<211> LENGTH: 364
<212> TYPE: PRT
<213> ORGANISM: Artificial Sequence
<220> FEATURE:
<223> OTHER INFORMATION: Description of Artificial Sequence:aligned aa
      sequence of Mycobacterium Mlep85c
<220> FEATURE:
<221> NAME/KEY: UNSURE
<222> LOCATION: (52)..(364)
<223> OTHER INFORMATION: Xaa is any amino acid.

-continued

```
<400> SEQUENCE: 15

Met Lys Phe Leu Gln Gln Met Arg Lys Leu Phe Gly Leu Ala Ala Lys
  1               5                  10                  15

Phe Pro Ala Arg Leu Thr Ile Ala Val Ile Gly Thr Ala Leu Leu Ala
                 20                  25                  30

Gly Leu Val Gly Val Val Gly Asp Thr Ala Ile Ala Val Ala Phe Ser
             35                  40                  45

Lys Pro Gly Xaa Leu Pro Val Glu Tyr Leu Gln Val Pro Ser Pro Xaa
         50                  55                  60

Ser Met Gly His Asp Ile Lys Ile Xaa Gln Phe Gly Gly Gly Gln
 65                  70                  75                  80

Xaa Xaa His Ala Val Tyr Leu Leu Asp Gly Leu Arg Ala Gln Glu Asp
                 85                  90                  95

Tyr Xaa Xaa Asn Gly Trp Asp Ile Asn Thr Pro Ala Phe Glu Glu Tyr
            100                 105                 110

Tyr His Ser Gly Xaa Leu Ser Val Ile Met Pro Val Gly Gly Gln Ser
            115                 120                 125

Ser Phe Tyr Ser Asn Trp Tyr Gln Pro Ser Gln Gly Asn Gly Gln His
130                 135                 140

Tyr Thr Tyr Lys Trp Glu Thr Xaa Phe Leu Thr Gln Glu Met Pro Ser
145                 150                 155                 160

Trp Leu Gln Ala Asn Lys Asn Val Leu Pro Thr Gly Asn Ala Ala Val
                165                 170                 175

Gly Leu Xaa Xaa Xaa Xaa Xaa Ser Met Gly Ser Ser Xaa Xaa
            180                 185                 190

Xaa Ala Leu Ile Leu Ala Ser Tyr Tyr Pro Gln Gln Phe Pro Xaa Xaa
        195                 200                 205

Xaa Tyr Ala Ala Ser Leu Ser Gly Phe Leu Asn Pro Ser Glu Gly Trp
    210                 215                 220

Trp Pro Thr Met Ile Gly Leu Ala Met Asn Asp Ser Gly Gly Tyr Asn
225                 230                 235                 240

Ala Asn Ser Met Trp Gly Pro Ser Thr Asp Pro Ala Trp Lys Arg Asn
                245                 250                 255

Asp Pro Met Val Gln Ile Pro Arg Leu Val Ala Asn Asn Thr Arg Ile
            260                 265                 270

Trp Val Tyr Cys Gly Asn Gly Ala Pro Asn Glu Leu Gly Gly Asp Asn
        275                 280                 285

Ile Pro Ala Lys Phe Leu Glu Ser Leu Thr Leu Ser Thr Asn Glu Ile
    290                 295                 300

Phe Gln Asn Thr Tyr Ala Ala Ser Gly Gly Arg Asn Gly Val Phe Asn
305                 310                 315                 320

Phe Pro Pro Asn Gly Thr His Ser Trp Pro Xaa Xaa Tyr Trp Asn Gln
                325                 330                 335

Gln Leu Val Ala Met Lys Pro Asp Ile Gln Gln Ile Leu Asn Gly Ser
            340                 345                 350

Asn Asn Asn Ala Xaa Xaa Xaa Xaa Xaa Xaa Xaa
        355                 360

<210> SEQ ID NO 16
<211> LENGTH: 364
<212> TYPE: PRT
<213> ORGANISM: Artificial Sequence
<220> FEATURE:
<223> OTHER INFORMATION: Description of Artificial Sequence:aligned aa
      sequence of Mycobacterium Mtu85b
```

<220> FEATURE:
<221> NAME/KEY: UNSURE
<222> LOCATION: (1)..(364)
<223> OTHER INFORMATION: Xaa is any amino acid.

<400> SEQUENCE: 16

```
Xaa Xaa Met Thr Asp Val Ser Arg Lys Ile Arg Ala Xaa Xaa Xaa Xaa
  1               5                  10                  15

Trp Gly Arg Arg Leu Met Ile Gly Thr Ala Ala Val Val Leu Pro
             20                  25                  30

Gly Leu Val Gly Leu Ala Gly Gly Ala Ala Thr Ala Gly Ala Phe Ser
             35                  40                  45

Arg Pro Gly Xaa Leu Pro Val Glu Tyr Leu Gln Val Pro Ser Pro Xaa
         50                  55                  60

Ser Met Gly Arg Asp Ile Lys Val Xaa Gln Phe Gln Ser Gly Gly Asn
 65                  70                  75                  80

Asn Ser Pro Ala Val Tyr Leu Leu Asp Gly Leu Arg Ala Gln Asp Asp
                 85                  90                  95

Tyr Xaa Xaa Asn Gly Trp Asp Ile Asn Thr Pro Ala Phe Glu Trp Tyr
            100                 105                 110

Tyr Gln Ser Gly Xaa Leu Ser Ile Val Met Pro Val Gly Gly Gln Ser
            115                 120                 125

Ser Phe Tyr Ser Asp Trp Tyr Ser Pro Ala Cys Gly Lys Ala Gly Cys
130                 135                 140

Gln Thr Tyr Lys Trp Glu Thr Xaa Phe Leu Thr Ser Glu Leu Pro Gln
145                 150                 155                 160

Trp Leu Ser Ala Asn Arg Ala Val Lys Pro Thr Gly Ser Ala Ala Ile
                165                 170                 175

Gly Leu Xaa Xaa Xaa Xaa Xaa Ser Met Ala Gly Ser Ser Xaa Xaa
            180                 185                 190

Xaa Ala Met Ile Leu Ala Ala Tyr His Pro Gln Gln Phe Ile Xaa Xaa
            195                 200                 205

Xaa Tyr Ala Gly Ser Leu Ser Ala Leu Leu Asp Pro Ser Gln Gly Met
    210                 215                 220

Gly Pro Ser Leu Ile Gly Leu Ala Met Gly Asp Ala Gly Gly Tyr Lys
225                 230                 235                 240

Ala Ala Asp Met Trp Gly Pro Ser Ser Asp Pro Ala Trp Glu Arg Asn
                245                 250                 255

Asp Pro Thr Gln Gln Ile Pro Lys Leu Val Ala Asn Asn Thr Arg Leu
            260                 265                 270

Trp Val Tyr Cys Gly Asn Gly Thr Pro Asn Glu Leu Gly Gly Ala Asn
            275                 280                 285

Ile Pro Ala Glu Phe Leu Glu Asn Phe Val Arg Ser Ser Asn Leu Lys
            290                 295                 300

Phe Gln Asp Ala Tyr Asn Ala Ala Gly Gly His Asn Ala Val Phe Asn
305                 310                 315                 320

Phe Pro Pro Asn Gly Thr His Ser Trp Glu Xaa Xaa Tyr Trp Gly Ala
                325                 330                 335

Gln Leu Asn Ala Met Lys Gly Asp Leu Gln Ser Ser Leu Xaa Gly Ala
            340                 345                 350

Gly Xaa Xaa Xaa Xaa Xaa Xaa Xaa Xaa Xaa
    355                 360
```

<210> SEQ ID NO 17
<211> LENGTH: 364

```
<212> TYPE: PRT
<213> ORGANISM: Artificial Sequence
<220> FEATURE:
<223> OTHER INFORMATION: Description of Artificial Sequence:aligned aa
      sequence of Mycobacterium Mlep85b
<220> FEATURE:
<221> NAME/KEY: UNSURE
<222> LOCATION: (1)..(364)
<223> OTHER INFORMATION: Xaa is any amino acid.

<400> SEQUENCE: 17
```

| | | | | | | | | | | | | | | |
|---|---|---|---|---|---|---|---|---|---|---|---|---|---|---|
| Xaa | Xaa | Met | Ile | Asp | Val | Ser | Gly | Lys | Ile | Arg | Ala | Xaa | Xaa | Xaa | Xaa |
| 1 | | | | 5 | | | | | 10 | | | | | 15 | |

Trp Gly Arg Trp Leu Leu Val Gly Ala Ala Thr Xaa Xaa Leu Pro
            20                  25              30

Ser Leu Ile Ser Leu Ala Gly Ala Ala Thr Ala Ser Ala Phe Ser
            35                  40              45

Arg Pro Gly Xaa Leu Pro Val Glu Tyr Leu Gln Val Pro Ser Glu Xaa
    50              55                  60

Ala Met Gly Arg Thr Ile Lys Val Xaa Gln Phe Gln Asn Gly Gly Asn
65                  70              75                  80

Gly Ser Pro Ala Val Tyr Leu Leu Asp Gly Leu Arg Ala Gln Asp Asp
                85                  90                  95

Tyr Xaa Xaa Asn Gly Trp Asp Ile Asn Thr Ser Ala Phe Glu Trp Tyr
            100                 105                 110

Tyr Gln Ser Gly Xaa Leu Ser Val Val Met Pro Val Gly Gly Gln Ser
        115                 120                 125

Ser Phe Tyr Ser Asp Trp Tyr Ser Pro Ala Cys Gly Lys Ala Gly Cys
    130                 135                 140

Thr Thr Tyr Lys Trp Glu Thr Xaa Phe Leu Thr Ser Glu Leu Pro Lys
145                 150                 155                 160

Trp Leu Ser Ala Asn Arg Ser Val Lys Ser Thr Gly Ser Ala Val Val
                165                 170                 175

Gly Leu Xaa Xaa Xaa Xaa Xaa Ser Met Ala Gly Ser Ser Xaa Xaa
                180                 185                 190

Xaa Ala Leu Ile Leu Ala Ala Tyr His Pro Asp Gln Phe Ile Xaa Xaa
    195                 200                 205

Xaa Tyr Ala Gly Ser Leu Ser Ala Leu Met Asp Ser Ser Gln Gly Ile
    210                 215                 220

Glu Pro Gln Leu Ile Gly Leu Ala Met Gly Asp Ala Gly Gly Tyr Lys
225                 230                 235                 240

Ala Ala Asp Met Trp Gly Pro Pro Asn Asp Pro Ala Trp Gln Arg Asn
            245                 250                 255

Asp Pro Ile Leu Gln Ala Gly Lys Leu Val Ala Asn Asn Thr His Leu
            260                 265                 270

Trp Val Tyr Cys Gly Asn Gly Thr Pro Ser Glu Leu Gly Gly Thr Asn
            275                 280                 285

Val Pro Ala Glu Phe Leu Glu Asn Phe Val His Gly Ser Asn Leu Lys
    290                 295                 300

Phe Gln Asp Ala Tyr Asn Gly Ala Gly Gly His Asn Ala Val Phe Asn
305                 310                 315                 320

Leu Asn Ala Asp Gly Thr His Ser Trp Glu Xaa Xaa Tyr Trp Gly Ala
                325                 330                 335

Gln Leu Asn Ala Met Lys Pro Asp Leu Gln Asn Thr Leu Xaa Met Ala
            340                 345                 350

Val Pro Arg Ser Gly Xaa Xaa Xaa Xaa Xaa Xaa Xaa

<210> SEQ ID NO 18
<211> LENGTH: 364
<212> TYPE: PRT
<213> ORGANISM: Artificial Sequence
<220> FEATURE:
<223> OTHER INFORMATION: Description of Artificial Sequence:aligned aa sequence of Mlep85a
<220> FEATURE:
<221> NAME/KEY: UNSURE
<222> LOCATION: (1)..(364)
<223> OTHER INFORMATION: Xaa is any amino acid.

<400> SEQUENCE: 18

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
           100                 105                 110

Xaa Xaa Xaa Xaa Xaa Xaa Xaa Xaa Xaa Xaa Xaa Xaa Xaa Xaa Xaa
       115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Leu Thr Ser Glu Leu Pro Gln
145                 150                 155                 160

Tyr Leu Gln Ser Asn Lys Gln Ile Lys Pro Thr Gly Ser Ala Ala Val
                165                 170                 175

Gly Leu Xaa Xaa Xaa Xaa Xaa Xaa Ser Met Ala Gly Leu Ser Xaa Xaa
            180                 185                 190

Xaa Ala Leu Thr Leu Ala Ile Tyr His Pro Asp Gln Phe Ile Xaa Xaa
        195                 200                 205

Xaa Tyr Val Gly Ser Met Ser Gly Leu Leu Asp Pro Ser Asn Ala Met
210                 215                 220

Gly Pro Ser Leu Ile Gly Leu Ala Met Gly Asp Ala Gly Gly Tyr Lys
225                 230                 235                 240

Ala Ala Asp Met Trp Gly Pro Ser Thr Asp Pro Ala Trp Lys Arg Asn
                245                 250                 255

Asp Pro Thr Val Asn Val Gly Thr Leu Ile Ala Asn Asn Thr Arg Ile
            260                 265                 270

Trp Met Tyr Cys Gly Asn Gly Lys Pro Thr Glu Leu Gly Gly Asn Asn
        275                 280                 285

Leu Pro Ala Lys Leu Leu Glu Gly Leu Val Arg Thr Ser Asn Ile Lys
290                 295                 300

Phe Gln Asp Gly Tyr Asn Ala Gly Gly His Asn Ala Val Phe Asn
305                 310                 315                 320

Phe Pro Asp Ser Gly Thr His Ser Trp Glu Xaa Xaa Tyr Trp Gly Glu
                325                 330                 335
```

```
Gln Leu Asn Asp Met Lys Pro Asp Leu Gln Gln Tyr Leu Xaa Gly Ala
            340                 345                 350

Thr Pro Gly Ala Xaa Xaa Xaa Xaa Xaa Xaa Xaa
            355                 360

<210> SEQ ID NO 19
<211> LENGTH: 364
<212> TYPE: PRT
<213> ORGANISM: Artificial Sequence
<220> FEATURE:
<223> OTHER INFORMATION: Description of Artificial Sequence:aligned aa
      sequence of adhesin seq14-19
<220> FEATURE:
<221> NAME/KEY: UNSURE
<222> LOCATION: (1)..(364)
<223> OTHER INFORMATION: Xaa is any amino acid.

<400> SEQUENCE: 19

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Ala
                 20                  25                  30

Gly Ser Thr Ser Val Ser Ala Ala Ser Ala Val Asn Ser Glu Leu Val
             35                  40                  45

His Lys Gly Glu Leu Thr Ile Gly Xaa Leu Glu Thr Tyr Ser Pro Tyr
 50                  55                  60

Ser Tyr Arg Lys Asn Asn Lys Leu Thr Gly Phe Glu Val Asp Gly Lys
 65                  70                  75                  80

Xaa Xaa Xaa Ala Val Ala Lys Lys Met Gly Leu Lys Ala Xaa Xaa Asn
                 85                  90                  95

Phe Val Pro Thr Lys Trp Ser Leu Xaa Ile Ala Gly Leu Gly Xaa Xaa
            100                 105                 110

Xaa Xaa Ser Gly Lys Phe Asp Val Val Met Xaa Xaa Xaa Xaa Xaa Xaa
            115                 120                 125

Xaa Xaa Xaa Asn Asn Ile Thr Thr Pro Glu Arg Ala Lys Gln Xaa Xaa
            130                 135                 140

Xaa Xaa Tyr Asn Phe Ser Thr Pro Tyr Ile Lys Ser Xaa Xaa Xaa Arg
145                 150                 155                 160

Phe Leu Xaa Xaa Xaa Xaa Xaa Ile Val Pro Thr Asp Ser Asn Ile Lys
            165                 170                 175

Ser Leu Lys Asn Ile Lys Gly Lys Lys Ile Ala Gly Thr Gly Thr Asn
            180                 185                 190

Asn Ala Asn Val Val Lys Lys Tyr Lys Gly Asn Leu Pro Asn Gly Asp
            195                 200                 205

Phe Ala Ser Ser Leu Xaa Asp Met Ile Lys Xaa Xaa Gln Gly Arg Xaa
            210                 215                 220

Xaa Xaa Xaa Xaa Xaa Xaa Xaa Xaa Xaa Xaa Ala Ala Gly Ile Asn Ser
225                 230                 235                 240

Arg Glu Ala Trp Tyr Xaa Xaa Xaa Xaa Ala Tyr Ser Lys Lys Xaa
            245                 250                 255

Xaa Xaa Xaa Xaa Xaa Xaa Xaa Xaa Xaa Asn Ser Thr Lys Xaa Xaa
            260                 265                 270

Xaa Xaa Xaa Gly Leu Gly Ile Xaa Xaa Asp Val Ser Ser Glu Gln Asp
            275                 280                 285

Pro Ala Lys Xaa Ile Ser Ala Leu Xaa Phe Asn Lys Asp Thr Ala Ile
            290                 295                 300
```

```
Gln Ser Ser Tyr Asn Xaa Xaa Xaa Xaa Xaa Lys Ala Leu Lys Glu Leu
305                 310                 315                 320

Gln Gln Asp Gly Val Lys Lys Leu Ser Glu Lys Tyr Phe Gly Ala Asp
                325                 330                 335

Ile Thr Glu Xaa Xaa Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa
                355                 360

<210> SEQ ID NO 20
<211> LENGTH: 364
<212> TYPE: PRT
<213> ORGANISM: Artificial Sequence
<220> FEATURE:
<223> OTHER INFORMATION: Description of Artificial Sequence:consensus of
      aligned aa sequences 14-19
<220> FEATURE:
<221> NAME/KEY: UNSURE
<222> LOCATION: (1)..(364)
<223> OTHER INFORMATION: Xaa is any amino acid.

<400> SEQUENCE: 20

Xaa Xaa Xaa Xaa Xaa Xaa Xaa Xaa Xaa Xaa Xaa Xaa Xaa Xaa Xaa Xaa
  1               5                   10                  15

Xaa Xaa Xaa Xaa Xaa Xaa Xaa Xaa Xaa Xaa Xaa Xaa Xaa Xaa Xaa Xaa
                20                  25                  30

Gly Xaa Xaa Xaa Xaa Xaa Xaa Xaa Ala Xaa Xaa Xaa Xaa Xaa
                35                  40                  45

Xaa Xaa Gly Xaa Leu Xaa Xaa Xaa Xaa Leu Xaa Xaa Xaa Ser Pro Xaa
         50                  55                  60

Ser Xaa Xaa Xaa Xaa Lys Xaa Xaa Xaa Phe Xaa Xaa Xaa Gly Xaa
 65                  70                  75                  80

Xaa Xaa Xaa Ala Val Xaa Xaa Xaa Xaa Gly Leu Xaa Ala Xaa Xaa Xaa
                85                  90                  95

Xaa Xaa Xaa Xaa Xaa Trp Xaa Xaa Xaa Xaa Xaa Xaa Xaa Xaa Xaa
                100                 105                 110

Xaa Xaa Ser Gly Xaa Xaa Xaa Val Val Met Xaa Xaa Xaa Xaa Xaa Xaa
            115                 120                 125

Xaa Xaa Xaa Xaa Asn Xaa Xaa Xaa Pro Xaa Xaa Lys Xaa Xaa Xaa
            130                 135                 140

Xaa Xaa Tyr Xaa Xaa Xaa Thr Xaa Xaa Xaa Xaa Ser Xaa Xaa Xaa Xaa
145                 150                 155                 160

Xaa Leu Xaa Xaa Xaa Xaa Xaa Xaa Xaa Pro Thr Xaa Ser Xaa Xaa Xaa
                165                 170                 175

Xaa Leu Xaa Xaa Xaa Xaa Xaa Xaa Xaa Ala Gly Xaa Xaa Xaa Xaa
                180                 185                 190

Xaa Ala Xaa Xaa Xaa Xaa Tyr Xaa Xaa Xaa Xaa Pro Xaa Xaa
            195                 200                 205

Xaa Xaa Ala Xaa Ser Leu Xaa Xaa Xaa Xaa Xaa Xaa Gln Gly Xaa
            210                 215                 220

Xaa Xaa Xaa Xaa Xaa Xaa Xaa Xaa Xaa Xaa Ala Xaa Gly Xaa Asn
225                 230                 235                 240

Xaa Xaa Xaa Xaa Trp Xaa Xaa Xaa Xaa Xaa Xaa Ala Xaa Xaa Xaa
                245                 250                 255

Xaa Xaa Xaa Xaa Xaa Xaa Xaa Xaa Xaa Xaa Asn Xaa Thr Xaa Xaa
                260                 265                 270

Xaa Xaa Xaa Xaa Gly Xaa Gly Xaa Xaa Xaa Asp Xaa Xaa Xaa Xaa Xaa
```

```
                275                 280                 285
Xaa Pro Ala Lys Xaa Xaa Xaa Leu Xaa Xaa Xaa Xaa Xaa Xaa
            290                 295                 300

Xaa Gln Xaa Xaa Tyr Asn Xaa Xaa Xaa Xaa Xaa Ala Xaa Xaa Xaa
305                 310                 315                 320

Leu Xaa Xaa Asp Gly Xaa Xaa Xaa Xaa Xaa Xaa Tyr Xaa Gly Ala
                325                 330                 335

Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa
            355                 360

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence:fragment of
      adhesin sequence=peptide I

<400> SEQUENCE: 21

Ala Ala Ser Ala Val Asn Ser Glu Leu Val His Lys
1               5                  10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence:fragment of
      adhesin sequence=peptide II

<400> SEQUENCE: 22

Ala Asn Phe Val Pro Thr Lys
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:fragment of
      adhesin sequence=peptide III

<400> SEQUENCE: 23

Asp Thr Ala Ile Gln Ser Ser Tyr Asn Lys
1               5                  10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:fragment of
      adhesin sequence=peptide IV

<400> SEQUENCE: 24

Ile Ser Ala Leu Phe Asn Lys
1               5

<210> SEQ ID NO 25
<211> LENGTH: 10
<212> TYPE: PRT
<213> ORGANISM: Artificial Sequence
<220> FEATURE:
```

```
<223> OTHER INFORMATION: Description of Artificial Sequence:fragment of
      adhesin sequence=peptide V
<220> FEATURE:
<221> NAME/KEY: UNSURE
<222> LOCATION: (10)
<223> OTHER INFORMATION: Xaa is any amino acid.

<400> SEQUENCE: 25

Ile Ala Gly Thr Gly Thr Asn Asn Ala Xaa
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence:N terminal
      fragment of adhesin sequence
<220> FEATURE:
<221> NAME/KEY: UNSURE
<222> LOCATION: (7)
<223> OTHER INFORMATION: Xaa is any amino acid.

<400> SEQUENCE: 26

Ala Xaa Xaa Ala Val Asn Xaa Glu Leu Val Val Lys
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence:fragment of
      adhesin sequence
<220> FEATURE:
<221> NAME/KEY: UNSURE
<222> LOCATION: (11)
<223> OTHER INFORMATION: Xaa is any amino acid.

<400> SEQUENCE: 27

Ile Ile Ala Gly Thr Gly Thr Asn Asn Ala Xaa
 1               5                  10

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:
      oligonucleotide 42 sense for N terminal adhesin sequence

<400> SEQUENCE: 28
ctgcgtaact tcgagattga gta                                           23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:
      oligonucleotide 105 antisense for peptide I

<400> SEQUENCE: 29
gccggtcctt tgtggacaat tgc                                           23

<210> SEQ ID NO 30
<211> LENGTH: 6
<212> TYPE: PRT
<213> ORGANISM: Artificial Sequence
```

-continued

```
<220> FEATURE:
<223> OTHER INFORMATION: Description of Artificial Sequence:consensus
      fragment of adhesin sequence
<220> FEATURE:
<221> NAME/KEY: UNSURE
<222> LOCATION: (3)..(5)
<223> OTHER INFORMATION: Xaa is any amino acid.

<400> SEQUENCE: 30

Lys Lys Xaa Xaa Xaa Lys
 1               5
```